United States Patent
Knop et al.

(10) Patent No.: US 9,783,826 B2
(45) Date of Patent: Oct. 10, 2017

(54) RECOMBINANT VIRUS PRODUCTION USING MAMMALIAN CELLS IN SUSPENSION

(71) Applicant: Applied Genetic Technologies Corporation, Alachua, FL (US)

(72) Inventors: David R. Knop, Gainesville, FL (US); Darby Thomas, Frederick, MD (US); Gabor Veres, Medford, MA (US)

(73) Assignee: Applied Genetic Technologies Corporation, Alachua, FL (US)

(*) Notice: Subject to any disclaimer, the term of this patent is extended or adjusted under 35 U.S.C. 154(b) by 0 days.

(21) Appl. No.: 13/683,577

(22) Filed: Nov. 21, 2012

(65) Prior Publication Data
US 2013/0244331 A1 Sep. 19, 2013

Related U.S. Application Data

(63) Continuation of application No. 12/812,671, filed on Jul. 13, 2010, now abandoned, which is a continuation of application No. PCT/US2009/000577, filed on Jan. 29, 2009.

(60) Provisional application No. 61/062,819, filed on Jan. 29, 2008.

(51) Int. Cl.
| | |
|---|---|
| *C12N 15/864* | (2006.01) |
| *C12N 15/869* | (2006.01) |
| *C12N 7/02* | (2006.01) |
| *C12N 15/87* | (2006.01) |
| *C07K 14/015* | (2006.01) |
| *C07K 14/005* | (2006.01) |
| *C12N 7/00* | (2006.01) |
| *C12N 15/86* | (2006.01) |
| *A61K 48/00* | (2006.01) |

(52) U.S. Cl.
CPC ........ *C12N 15/8645* (2013.01); *C07K 14/005* (2013.01); *C12N 7/00* (2013.01); *C12N 15/86* (2013.01); *A61K 48/00* (2013.01); *C12N 2710/16643* (2013.01); *C12N 2710/16662* (2013.01); *C12N 2750/14122* (2013.01); *C12N 2750/14143* (2013.01); *C12N 2800/50* (2013.01)

(58) Field of Classification Search
None
See application file for complete search history.

(56) References Cited

U.S. PATENT DOCUMENTS

| | | | | |
|---|---|---|---|---|
| 5,723,031 A | * | 3/1998 | Durr | ........................ C12Q 1/04 204/451 |
| 6,686,200 B1 | * | 2/2004 | Dong et al. | .................... 435/457 |
| 6,793,926 B1 | | 9/2004 | Rasty et al. | |
| 7,037,723 B1 | | 5/2006 | Helibronn | |
| 2003/0159978 A1 | * | 8/2003 | Self et al. | ..................... 210/163 |
| 2007/0202587 A1 | * | 8/2007 | Hwang et al. | ............. 435/235.1 |
| 2011/0014232 A1 | * | 1/2011 | Maree | .................. C07K 14/005 424/216.1 |

OTHER PUBLICATIONS

Booth et al, Transfection-free and scalable recombinant AAV vector production using HSV/AAV hybrids, Gene Therapy (2004) 11,829-837.*
Gibco, CD BHK-21 Production Medium, Publication No. MAN 009637, pp. 1-2.*
Gibco, CD BHK-21 Production Medium, Publication No. MAN 009637, 2013, pp. 1-2.*
Clement N., et al., Large-scale adeno-associated viral vector production using a herpesvirus-based system enables manufacturing for clincal studies. Hum Gene Ther. Aug. 2009;20(8):796-806.
Durocher Y, et al., Scalable serum-free production of recombinant adeno-associated virus type 2 by transfection of 293 suspension cells. J Virol Methods. Sep. 2007; 144(1-2):32-40.
Extended European Search Report for EP09706778.9/2242840 PCT/US2009000577. Dated Nov. 21, 2012.
Hildinger M., et al., High-titer, serum-free production of adeno-associated virus vectors by polyethyleneimine-mediated plasmid transfection in mammalian suspension cells.Biotechnol Lett. Nov. 2007;29(11):1713-21.
Knop D.R., et al., Bioreactor production of recombinant herpes simplex virus vectors. Biotechnol Prog. May-Jun. 2007;23(3):715-21.
Park J.Y.., et al., Scalable production of adeno-associated virus type 2 vectors via suspension transfection Biotechnol Bioeng. Jun. 20, 2006;94(3):416-30.
Perrin P., et al., An experimental rabies vaccine produced with a new BHK-21 suspension cell culture process: use of serum-free medium and perfusion-reactor system. Vaccine. Sep. 1995;13(13):1244-50.
Thomas DL., et al., Scalable recombinant adeno-associated virus production using recombinant herpes simplex virus type 1 coinfection of suspension-adapted mammalian cells. Hum Gene Ther. Aug. 2009;20(8):861-70.
Wurm FM. Production of recombinant protein therapeutics in cultivated mammalian cells. Nat Biotechnol. Nov. 2004;22(11):1393-1398.

* cited by examiner

*Primary Examiner* — Maria Marvich
(74) *Attorney, Agent, or Firm* — McCarter & English, LLP; Jonathan M. Sparks

(57) ABSTRACT

The invention generally provides methods for producing recombinant AAV viral particles using cells grown in suspension. The invention provides recombinant AAV particles for use in methods for delivering genes encoding therapeutic proteins, and methods for using the recombinant AAV particles in gene therapy.

9 Claims, 14 Drawing Sheets

RECOMBINANT VIRUS PRODUCTION USING MAMMALIAN CELLS IN SUSPENSION

RELATED APPLICATIONS

This application is a continuation of U.S. patent application Ser. No. 12/812,671, filed on Jul. 13, 2010, now abandoned, which is a continuation of International Application No. PCT/US2009/000577, filed Jan. 29, 200920009, which claims benefit of U.S. Provisional Patent Application No. 61/062,819, filed Jan. 29, 2008. The entire contents of each of the above documents is herein incorporated by reference in their entirety.

BACKGROUND OF THE INVENTION

The present invention relates to the field of viral based gene therapy, in particular to recombinant adeno-associated virus (rAAV) based gene therapy. The invention relates to methods for producing recombinant AAV viral particles using cells grown in suspension. The invention provides recombinant AAV particles for use in methods for delivering genes encoding therapeutic proteins, and methods for using the recombinant AAV particles in in vivo or in ex vivo gene therapy.

The present invention seeks to overcome some of the deficiencies in the prior art by addressing problems that limit production of rAAV vectors in sufficient quantities for efficient gene therapy procedures. It is apparent from the foregoing that there is a clear need for improved large-scale methods for production of high titer infectious rAAV and improved production methods can include different techniques to make production more efficient.

Using methods and materials disclosed herein, infectious rAAV can be obtained in mammalian cell lines grown in suspension including those that have not been genetically altered by recombinant genetic engineering for improved rAAV production.

SUMMARY OF THE INVENTION

The present invention seeks to overcome some of the deficiencies in the prior art by addressing problems that limit production of rAAV in sufficient quantities for clinical and commercial application. Because the quantity of virus that is required for clinical application, an efficient and scalable method of virus production is required. This invention provides an efficient and scalable method for producing recombinant AAV viral particles by utilizing cells grown in suspension.

The invention is based, in part, on a novel method for producing high titer rAAV as described in U.S. application Ser. No. 11/503,775, entitled Recombinant AAV Production in Mammalian Cells, filed Aug. 14, 2007, which is a continuation-in-part of U.S. application Ser. No. 10/252,182, entitled High Titer Recombinant AAV Production, filed Sep. 23, 2002, now U.S. Pat. No. 7,091,029, issued Aug. 15, 2006. The contents of all the aforementioned applications are hereby incorporated by reference in their entirety.

In the method described herein, mammalian cells are simultaneously or sequentially co-infected within several hours with at least two recombinant, herpes simplex viruses (rHSV). The two rHSV are vectors designed to provide the cells, upon infection, with all of the components necessary to produce rAAV. The method does not require the use of mammalian cells specialized for expression of particular gene products. This is advantageous because the invention can be practiced using any mammalian cell generally suitable for this purpose.

Examples of suitable genetically unmodified mammalian cells include but are not limited to cell lines such as HEK-293 (293), Vera, RD, BHK-21, HT-1080, A549, Cos-7, ARPE-19, and MRC-5.

In a first aspect, the invention features a method for producing recombinant AAV viral particles in a mammalian cell comprising co-infecting a mammalian cell capable of growing in suspension with a first recombinant herpesvirus (rHSV) comprising a nucleic acid encoding an AAV rep and an AAV cap gene each operably linked to a promoter; and (ii) a second rHSV comprising a gene of interest, and a promoter operably linked to said gene of interest; and allowing the virus to infect the mammalian cell; thereby producing recombinant AAV viral particles in a mammalian cell.

In one embodiment, the gene of interest is a therapeutic gene.

In another embodiment, the therapeutic gene is selected from the group consisting of: an angiogenesis inhibiting gene (AT), alpha-1 antitrypsin, retinoschisin, acid alpha glucosidase, and RPE65, In certain embodiments, the angiogenesis inhibiting gene is sFlt01.

In a further embodiment, the AAV cap gene has a serotype selected from the group consisting of AAV-1, AAV-2, AAV-3, AAV-4, AAV-5, AAV-6, AAV-7, and AAV-8, AAV-9, and rh-AAV-10.

In another aspect, the invention features a method for producing recombinant AAV viral particles in a mammalian cell comprising co-infecting a mammalian cell capable of growing in suspension with a first recombinant herpesvirus comprising a nucleic acid encoding an AAV rep2 and an AAV cap1 or cap 2 gene each operably linked to a promoter; and (ii) a second recombinant herpesvirus comprising a therapeutic gene like an alpha 1 antitrypsin gene, and a promoter operably linked to said gene; and allowing the virus to infect the mammalian cell, thereby producing recombinant AAV viral particles in a mammalian cell.

In one embodiment of the aspects described above, the mammalian cell is selected from the group consisting of: BHK, HEK-293 (293), Vero, RD, HT-1080, A549, Cos-7, ARPE-19, and MRC-5.

In another aspect, the invention features a method for producing recombinant AAV viral particles in a BHK cell comprising co-infecting a BHK cell capable of growing in suspension with a first recombinant herpesvirus comprising a nucleic, acid encoding an AAV rep and an AAV cap gene each operably linked to a promoter; and (ii) a second recombinant herpesvirus comprising a gene of interest, and a promoter operably linked to said gene of interest; and allowing the virus to infect the BHK cell; thereby producing recombinant AAV viral particles in a BHK cell.

In yet another aspect the invention features a method for producing recombinant viral particles in a BHK cell comprising co-infecting a BHK cell capable of growing in suspension with a first recombinant herpesvirus comprising a nucleic acid encoding an AAV rep2 and an AAV cap1, -2, -5, or -8 gene each operably linked to a promoter; and (ii) a second recombinant herpesvirus comprising an AI gene or an alpha 1 antitrypsin gene, and a promoter operably linked to said gene of interest; and allowing the virus to infect the BHK cell; thereby producing recombinant viral particles in a BHK cell.

In an embodiment of the method of any one of the above-mentioned claims, the herpesvirus is a virus selected from the group herpesviridae consisting of cytomegalovirus (CMV), herpes simplex (HSV), varicella zoster (VZV), and epstein barr virus (EBV), Kaposi sarcoma-associated virus (KSHV), human herpesvirus 6a and 6b (HHV6a and HHV6b), and human herpesvirus 7 (HHV7).

In another embodiment, the herpesvirus is replication defective.

In another embodiment, the gene of interest is a therapeutic gene.

In a further embodiment, the therapeutic gene is selected from the group consisting of an anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc finger, nucleic acid binding protein (known as CNBP or ZNF9), Retinitis pigmentosa GTPase regulator (RPGR), Acid α-glucosidase (GAA), Choroideremia (CHM), Rab escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase.

In still another embodiment, the AAV cap gene has a serotype selected from the group consisting of AAV-1, AAV-2, AAV-3, AAV-4, AAV-5, AAV-6, AAV-7, AAV-8, AAV-9, and rhAAV-10.

In another embodiment of any one of the above-mentioned aspects, the method further comprises the step of determining multiplicity of infection (MOI). In a related embodiment, the total MOI is between 3 and 14.

In one embodiment of any one of the above-mentioned aspects, the co-infection is simultaneous.

In another aspect, the invention features a method for producing recombinant viral particles in a BHK cell comprising simultaneously co-infecting a BHK cell capable of growing in suspension with a first recombinant Herpes Family virus comprising a nucleic acid encoding an AAV rep and an AAV cap gene each operably linked to a promoter; and (ii) a second recombinant Herpes Family virus comprising a gene of interest, and a promoter operably linked to said gene of interest, allowing the virus to infect the BHK cell; and purifying the viral particles, thereby producing recombinant viral particles in a BHK cell.

In a further aspect, the invention features a method for producing recombinant viral particles in a BHK cell comprising simultaneously co-infecting a BHK cell capable of growing in suspension with a first recombinant herpesvirus comprising a nucleic acid encoding an AAV rep and an AAV cap gene each operably linked to a promoter; and (ii) a second recombinant herpesvirus comprising an AI gene or an alpha 1 antitrypsin gene, and a promoter operably linked to said gene of interest, allowing the virus to infect the BHK cell; and purifying the viral particles; thereby producing recombinant viral particles in a BHK cell.

In one embodiment of the above aspects, the herpesvirus is a virus selected from the group consisting of HSV-1, HSV-2, HHV-3, HHV-4, HHV-5, HHV-6, HHV-7, HHV-8, In a further embodiment, the herpesvirus is a human herpesvirus selected from the group consisting of: human herpesviruses types 1, 2, 3, 4, 5, 6A, 6B, 7, and 8.

In another embodiment, the recombinant herpesvirus is replication defective.

In a further embodiment, the gene of interest is a therapeutic gene.

In another further embodiment, the therapeutic gene is selected from the group consisting of: anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc finger, nucleic acid binding protein (known as CNBP or ZNF9), Retinitis pigmentosa GTPase regulator (RPGR), Acid α-glucosidase (GAA), Choroideremia (CHM), Rab escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase.

In still another embodiment, the AAV cap gene has a serotype selected from the group consisting of AAV-1, AAV-2, AAV-3, AAV-4, AAV-5, AAV-6, AAV-7, AAV-8, AAV-9, and rhAAV-10.

In another embodiment, the invention features a method for producing recombinant viral particles in a mammalian cell according to any one of the aspects as described above, whereby the number of viral particles produced is equal to or greater than the number of viral particles grown in an equal number of cells under adherent conditions.

In another aspect, the invention features a recombinant AAV viral particle produced in a mammalian cell by the method comprising co-infecting a mammalian cell capable of growing in suspension with a first recombinant herpesvirus comprising a nucleic acid encoding an AAV rep and an AAV cap gene each operably linked to a promoter; and (ii) a second recombinant herpesvirus comprising a gene of interest, and a promoter operably linked to said gene of interest; and allowing the virus to infect the mammalian cell; thereby producing recombinant AAV viral particles in a mammalian cell.

In one embodiment, the herpesvirus is a virus selected from the group consisting of: cytomegalovirus (CMV), herpes simplex (HSV) and varicella zoster (VZV) and epstein barr virus (EBV).

In another embodiment, the recombinant herpesvirus is replication defective.

In still another embodiment, the gene of interest is a therapeutic gene.

In yet another further embodiment, the therapeutic gene is selected from the group consisting of: anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc linger, nucleic acid binding protein (known as CNBP or ZNF9), Retinitis pigmentosa GTPase regulator (RPGR), Acid α-glucosidase (GAA), Choroideremia (CHM), Rah escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase.

In another embodiment, the gene of interest is a reporter gene.

In a further embodiment, the AAV cap gene has a serotype selected from the group consisting of AAV-1, AAV-2, AAV-3, AAV-4, AAV-5, AAV-6, AAV-7, AAV-8, AAV-9, and rhAAV-10.

In another aspect, the invention features a recombinant AAV viral particle produced in a BHK cell comprising co-infecting a BHK cell capable of growing in suspension with a first recombinant herpesvirus comprising a nucleic acid encoding an AAV rep and an AAV cap gene each operably linked to a promoter; and (ii) a second herpesvirus comprising a gene of interest, and a promoter operably linked to said gene of interest; and allowing the virus to infect the BHK cell; thereby producing recombinant AAV viral particles in a BHK cell.

In another aspect, the invention features a method for delivering a nucleic acid sequence encoding a therapeutic protein to a target cell, the method comprising co-infecting a mammalian cell capable of growing in suspension with a first recombinant herpesvirus comprising a nucleic acid encoding an AAV rep and an AAV cap gene each operably linked to a promoter; and (ii) a second herpesvirus comprising a gene of interest, wherein the gene of interest comprises a therapeutic gene, and a promoter operably linked to said gene of interest; and allowing the virus to infect the mammalian cell and express the nucleic acid sequence encoding a therapeutic protein; thereby delivering a nucleic acid sequence encoding a therapeutic protein to the target cell.

In one embodiment, the herpesvirus is a virus selected from the group consisting of: cytomegalovirus (CMV), herpes simplex (HSV) and varicella zoster (VZV) and epstein barr-virus (EBV).

In another embodiment, the recombinant Herpes Family virus is replication defective.

In a further embodiment, the gene of interest is a therapeutic gene.

In still another embodiment, the therapeutic gene is selected from the group consisting of: anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment, epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc finger, nucleic acid binding protein (known as CNBP or ZNF9), Retinitis pigmentosa GTPase regulator (RPGR), Acid α-glucosidase (GAA), Choroideremia (CHM), Rab escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase.

In a further embodiment, the AAV cap gene has a serotype selected from the group consisting of AAV-1, AAV-2, AAV-3, AAV-4, AAV-5, AAV-6, AAV-7, AAV-8, AAV-9, and rhAAV-10.

In another aspect, the invention features a kit for making a recombinant viral particle in a mammalian cell that is capable of growing in suspension, and instructions for use.

In yet another aspect, the invention features a kit for delivering a nucleic acid sequence encoding a therapeutic protein to a target cell according to claim 33, and instructions for use.

BRIEF DESCRIPTION OF THE DRAWINGS

FIG. 4A shows cumulative data for experiments examining rAAV production with rHSV-rep2cap2 used in co-infections over the indicated range of MOIs. All co-infections were performed with rHSV-GFP used at an MOI of 2 and cells were infected at densities ranging from $8.13 \times 10^5$ to $3.76 \times 10^6$ cells/mL. Two hours post-infection, cells were pelleted and resuspended in DMEM without FBS. Samples were harvested by in situ lysis between 18 and 48 hpi and were assayed for the level of rAAV2-GFP production by the green-cell infectivity assay. The numbers inside the bars represent the number of flasks assayed at the indicated MOI. Error bars represent inter-assay variation. FIG. 4B shows DNAse-resistant particle (DRP) and ip production by sBHK cells with rHSV-rep2cap2 used at varying MOIs. Representative samples (n=2) from graph A were also assayed for the level of DRP produced (line). The mean ip/cell of those samples is presented as well (bars). The mean DRP to ip ratio is 13.8 (+/−3.2) to 1.

DETAILED DESCRIPTION OF THE INVENTION

Figure 1:
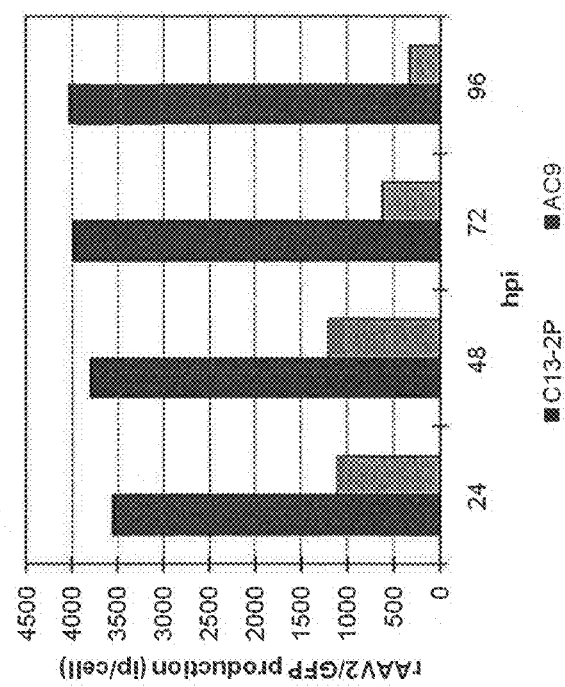
FIG. 1 is a graph that shows a comparison of rAAV production by two different isolates of suspension BHK cells. Suspension BHK isolates C13-2P ($4.5 \times 10^5$ cells/mL) and AC9 ($4.7 \times 10^5$ cells/mL) were co-infected with rHSV-rep2cap2 and rHSV-GFP at a multiplicity of infection (MOI) of 12 and 2, respectively. Samples of the production over time were assayed for the level of rAAV2-GFP production by the green-cell infectivity assay.

The invention generally provides methods for producing recombinant AAV viral particles, using cells grown in suspension, and their use in methods of gene therapy.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

As used herein, the term "gene" or "coding sequence" refers to a DNA region (the transcribed region) which encodes a protein. A coding sequence is transcribed (DNA) and translated (RNA) into a polypeptide when placed under the control of an appropriate regulatory region, such as a promoter. A gene may comprise several operably linked fragments, such as a promoter, a 5'leader sequence, a coding sequence and a 3'nontranslated sequence, comprising a polyadenylation site. The phrase "expression of a gene" refers to the process wherein a gene is transcribed into an RNA and/or translated into an active protein.

The term "gene of interest" (GOI) is meant to refer to a heterologous sequence introduced into an AAV expression vector, and typically refers to a nucleic acid sequence encoding a protein of therapeutic use in humans or animals.

The term "herpesvirus" or "herpesviridae family" is meant to refer to the general family of enveloped, double-stranded DNA viruses with relatively large genomes. The family replicates in the nucleus of a wide range of vertebrate and invertebrate hosts, in preferred embodiments, mammalian hosts, for example in humans, horses, cattle, mice, and pigs. Exemplary members of the herpesviridae family include cytomegalovirus (CMV), herpes simplex virus types 1 and 2 (HSV1 and HSV2) and varicella zoster (VZV) and epstein barr virus (EBV).

The term "infection" is meant to refer to delivery of heterologous DNA into a cell by a virus. The term "co-infection" as used herein means "simultaneous infection," "double infection," "multiple infection," or "serial infection" with two or more viruses. Infection of a producer cell with two (or more) viruses will be referred to as "co-infection." The term "transfection" refers to a process of delivering heterologous DNA to a cell by physical or chemical methods, such as plasmid DNA, which is transferred into the cell by means of electroporation, calcium phosphate precipitation, or other methods well known in the art.

The terms "recombinant HSV," "rHSV," and "rHSV vector" refer to isolated, genetically modified forms of herpes simplex virus type 1 (HSV) containing heterologous genes incorporated into the viral genome. By the term "rHSV-rep2cap2" or "rHSV-rep2cap1" is meant an rHSV in which the AAV rep and cap genes from either AAV serotype 1 or 2 have been incorporated into the rHSV genome, in certain embodiments, a DNA sequence encoding a therapeutic gene of interest has been incorporated into the viral genome.

The term "AAV virion" refers to a complete virus particle, such as for example a wild type AAV virion particle, which comprises single stranded genome DNA packaged into AAV capsid proteins. The single stranded nucleic acid molecule is either sense strand or antisense strand, as both strands are equally infectious. The term "rAAV viral particle" refers to a recombinant AAV virus particle, i.e. a particle that is infectious but replication defective. A rAAV viral particle comprises single stranded genome DNA packaged into AAV capsid proteins.

The term "therapeutic protein" as used herein refers to a protein, which has a therapeutic effect on a disease or disorder to be treated. The therapeutic protein, when expressed in an effective amount (or dosage) is sufficient to prevent, correct and/or normalize an abnormal physiological response. For example, a therapeutic protein may be sufficient to reduce by at least about 30 percent, more preferably by at least 50 percent, most preferably by at least 90 percent, a clinically significant feature of disease or disorder.

As used herein, the term "transgene" refers to a heterologous gene(s), or recombinant genes ("gene cassette") in a vector, which is transduced into a cell. Use of the term "transgene" encompasses both introduction of the gene or gene cassette for purposes of correcting a gene defect, in the cell, or altering the functions of the transduced and/or surrounding cells, and introduction of the gene or gene cassette into a producer cell for purposes of enabling the cell to produce rAAV. In certain embodiments, introducing the gene or gene cassette for the purposes of correcting a gene defect in the cell or altering the functions of the transduced and/or surrounding cells can be earned out by gene therapy. By the term "vector" is meant a recombinant plasmid or viral construct used as a vehicle for introduction of transgenes into cells.

Adeno-Associated Virus (AAV)

Adeno-Associated Virus (AAV) is a non-pathogenic single-stranded DNA parvovirus. AAV has a capsid diameter of about 20 nm. Each end of the single-stranded DNA genome contains an inverted terminal repeat (ITR), which is the only cis-acting element required for genome replication and packaging. The AAV genome carries two viral genes: rep and cap. The virus utilizes two promoters and alternative splicing to generate four proteins necessary for replication (Rep 78, Rep 68, Rep 52 and Rep 40). A third promoter generates the transcript for three structural viral capsid proteins, 1, 2 and 3 (VP1, VP2 and VP3), through a combination of alternate splicing and alternate translation start codons (Berns K I, Linden R M. The cryptic life style of adeno-associated virus. Bioessays. 1995; 17:237-45). The three capsid proteins share the same C-terminal 533 amino acids, while VP2 and VP1 contain additional N-terminal sequences of 65 and 202 amino acids, respectively. The AAV virion contains a total of 60 copies of VP1, VP2, and VP3 at a 1:1:20 ratio, arranged in a T-1 icosahedral symmetry (Rose J A, Maizel J V Jr, Inman J K, Shatkin A J. Structural proteins of adenovirus-associated viruses. J Virol. 1971; 8:766-70). AAV requires Adenovirus (Ad), Herpes Simplex Virus (HSV) or other viruses as a helper virus to complete its lytic life-cycle (Atchison R W, Casto B C, Hammon W M. Adenovirus-Associated Defective Virus Particles, Science, 1965; 149:754-6; Hoggan M D, Blacklow N R, Rowe W P. Studies of small DNA viruses found in various adeno-virus preparations: physical, biological, and immunological characteristics. Proc Natl Acad Sci USA, 1966; 55:1467-74). In the absence of the helper virus, wt AAV establishes latency by integration with the assistance of Rep proteins through the interaction of the ITR with the chromosome (Berns et al., 1995).

AAV Serotypes

There are a number of different AAV serotypes, including AAV-1, AAV-2, AAV-3, AAV-4, AAV-5, AAV-6, AAV-7, and AAV-8, AAV-9, and rh-AAV-10. In vivo studies have shown that the various AAV serotypes display different tissue or cell tropisms. For example, AAV-1 and AAV-6 are two serotypes that, are efficient for the transduction of skeletal muscle (Gao G P, Alvira M R, Wang L, et al. Novel adeno-associated viruses from rhesus monkeys as vectors for human gene therapy. Proc Natl Acad Sci USA, 2002; 99:11854-11859; Xiao W, Chirmule N, Berta S C, et al. Gene therapy vectors based on adeno-associated virus type 1. J Virol. 1999; 73:3994-4003; Chao H, Liu Y, Rabinowitz J, et al. Several log increase in therapeutic transgene delivery by distinct adeno-associated viral serotype vectors. Mol Ther. 2000; 2:619-623). AAV-3 has been shown to be superior for the transduction of megakaryocytes (Handa A, Muramatsu S, Qiu J, Mizukami H, Brown K E. Adeno-associated virus (AAV)-3-based vectors transduce haematopoietic cells not susceptible to transduction with AAV-2-based vectors, J Gen Virol. 2000; 81:2077-2084). AAV-5 and AAV-6 infect apical airway cells efficiently (Zabner J, Seller M, Walters R, et al, Adeno-associated virus type 5 (AAV5) but not AAV2 binds to the apical surfaces of airway epithelia and facilitates gene transfer. J Virol. 2000; 74:3852-3858; Halbert C L, Allen J M, Miller A D. Adeno-associated virus type 6 (AAV6) vectors mediate efficient transduction of airway epithelial cells in mouse lungs compared to that of AAV2 vectors. J Virol. 2001; 75:6615-6624.). AAV-2, AAV-4, and AAV-5 transduce different types of cells in the central nervous system (Davidson B L. Stein C S, Heth J A, et al. Recombinant adeno-associated virus type 2, 4, and 5 vectors: transduction of variant cell types and regions in the mammalian central nervous system. Proc Natl Acad Sci USA. 2000; 97:3428-3432). AAV-8 and AAV-5 can transduce liver cells better than AAV-2 (Gao G P, Alvira M R, Wang L, et al. Novel adeno-associated viruses from rhesus monkeys as vectors for human gene therapy. Proc Natl Acad Sci USA. 2002; 99:11854-11859; Mingozzi F, Schuttrampf J, Arruda V R, et al. Improved hepatic gene transfer by using an adeno-associated virus serotype 5 vector. J Virol. 2002; 76:10497-10502). WO99/61601, incorporated by reference in its entirety herein, shows that AAV5 based vectors transduced certain cell types (cultured airway epithelial cells, cultured striated muscle cells and cultured human umbilical vein endothelial cells) at a higher efficiency than AAV2, while both AAV2 and AAV5 showed poor transduction efficiencies for NIH 3T3, skbr3 and t-47D cell lines. AAV-4 was found to transduce rat retina most efficiently, followed by AAV-5 and AAV-1 (Rabinowitz J E, Rolling F, Li C, et al. Cross-packaging of a single adeno-associated virus (AAV) type 2 vector genome into multiple AAV serotypes enables transduction with broad specificity. J Virol. 2002; 76:791-801; Weber M, Rabinowitz J, Provost. N, et al. Recombinant adeno-associated virus serotype 4 mediates unique and exclusive long-term transduction of retinal pigmented epithelium in rat, dog, and nonhuman primate after subretinal delivery. Mol Ther. 2003; 7:774-781).

Since the development of naturally occurring AAV serotypes into gene therapy vectors, much effort has been focused towards understanding the tropism of each serotype so that further modification to the virus could be performed to enhance the efficiency of gene transfer. One approach is to swap domains from one serotype capsid to another, and thus create hybrid vectors with desirable qualities from each parent. As the viral capsid is responsible for cellular receptor binding, the understanding of viral capsid domain(s) critical for binding is important. Mutation studies on the viral capsid (mainly on AAV2) performed before the availability of the crystal structure were mostly based on capsid surface functionalization by adsorption of exogenous moieties, insertion of peptide at a random position, or comprehensive mutagenesis at the amino acid level. Choi et al. (Curr Gene Ther. 2005 June; 5(3): 299-310), incorporated by reference in its entirety herein, describe different approaches and considerations for hybrid serotypes.

The invention includes a method for producing rAAV particles with capsid proteins expressed by multiple serotypes of AAV. This is achieved by co-infection of producer cells with a rHSV expression virus and with a rHSV-rep2capX helper virus in which the cap gene products are derived from serotypes of AAV other than, or in addition to, AAV2. Recombinant AAV vectors have generally been based on AAV-2 capsids. It has recently been demonstrated that rAAV vectors based on capsids from AAV-1, AAV-3, AAV-4, AAV-5, AAV-8 or AAV-9 serotypes differ from AAV-2 in their tropism.

Capsids from other AAV serotypes offer advantages in certain in vivo applications over rAAV vectors based on the AAV-2 capsid. First, the appropriate use of rAAV vectors with particular serotypes may increase the efficiency of gene delivery in vivo to certain target cells that are poorly infected, or not infected at all, by AAV-2 based vectors. Secondly, it may be advantageous to use rAAV vectors based on other AAV serotypes if re-administration of rAAV vector becomes clinically necessary. It has been demonstrated that re-administration of the same rAAV vector with the same capsid can be ineffective, possibly due to the generation of neutralizing antibodies generated to the vector (Xiao, et al., 1999, Halbert, et al., 1997). This problem may be avoided by administration of a rAAV particle whose capsid is composed of proteins from a different AAV serotype, not affected by the presence of a neutralizing antibody to the first rAAV vector (Xiao, et al., 1999). For the above reasons, recombinant AAV vectors constructed using cap genes from serotypes including and in addition to AAV-2 are desirable. It will be recognized that the construction of recombinant HSV vectors similar to rHSV but encoding the cap genes from other AAV serotypes (e.g. AAV-1, AAV-2, AAV-3, AAV-5 to AAV-9) is achievable using the methods described herein to produce rHSV, In certain preferred embodiments of the invention as described herein, recombinant AAV vectors constructed using cap genes from different AAV are preferred. The significant advantages of construction of these additional rHSV vectors are ease and savings of time, compared with alternative methods used for the large-scale production of rAAV. In particular, the difficult process of constructing new rep and cap inducible cell lines for each different capsid serotypes is avoided.

AAV and Gene Therapy

Gene therapy refers to treatment of inherited or acquired diseases by replacing, altering, or supplementing a gene responsible for the disease. It is achieved by introduction of a corrective gene or genes into a host cell, generally by means of a vehicle or vector. Gene therapy using rAAV holds great promise for the treatment of many diseases. The invention provides a novel method of producing recombinant adeno-associated virus (rAAV), and in particular producing large quantities of recombinant AAV, to support clinical applications.

To date more than 500 gene therapy clinical trials have been conducted worldwide. Efforts to use rAAV as a vehicle for gene therapy hold promise for its applicability as a treatment for human diseases. Already, some success has been achieved pre-clinically, using recombinant AAV (rAAV) for the delivery and long-term expression of introduced genes into cells in animals, including clinically important non-dividing cells of the brain, liver, skeletal muscle and lung. In some tissues, AAV vectors have been shown to integrate into the genome of the target cell (Hirata et al. 2000, J. of Virology 74:4612-4620).

An additional advantage of rAAV is its ability to perform this function in non-dividing cell types including hepatocytes, neurons and skeletal myocytes. rAAV has been used successfully as a gene therapy vehicle to enable expression of erythropoietin in skeletal muscle of mice (Kessler et al., 1996), tyrosine hydroxylase and aromatic amino acid decarboxylase in the CNS in monkey models of Parkinson disease (Kaplitt et al., 1994) and Factor IX in skeletal muscle and liver in animal models of hemophilia. At the clinical level, the rAAV vector has been used in human clinical trials to deliver the CFTR gene to cystic fibrosis patients and the Factor IX gene to hemophilia patients (Flotte, et al., 1998, Wagner et al, 1998), Further, AAV is a helper-dependent DNA parvovirus, which is not associated with disease in humans or mammals (Berns and Bohensky, 1987, Advances in Virus Research, Academic Press Inc, 32:243-307). Accordingly, one of the most important attributes of AAV vectors is their safety profile in phase I clinical trials.

AAV gene therapy has been carried out in a number of different pathological settings and to treat a various diseases and disorders. For example, in a phase I study, administration of an AAV2-FIX vector into the skeletal muscle of eight hemophilia B subjects proved safe and achieved local gene transfer and Factor IX expression for at least 10 months after vector injection (Jiang et al, Mol Ther. 2006 September; 14(3):452-5. Epub 2006 July 5), a phase I trial of intramuscular injection of a recombinant adeno-associated virus alpha 1-antitrypsin (rAAV2-CB-hAAT) gene vector to AAT-deficient adults has been described previously (Flotte et al., Hum Gene Ther. 2004 January; 15(1):93-128), and in another clinical trial AA V-GAD gene therapy of the subthalamic nucleus has been shown to be safe and well tolerated by patients with advanced Parkinson's disease (Kaplitt et al. Lancet. 2007 June 23; 369(9579):2097-105).

Conventional AAV production methodologies make use of procedures known to limit the number of rAAV that a single producer cell can make. The first of these is transfection using plasmids for delivery of DNA to the cells. It is well known that plasmid transfection is an inherently inefficient process requiring high genome copies and therefore large amounts of DNA (Hauswirth et al., 2000).

Advances toward achieving the desired goal of scalable production systems that can yield large quantities of clinical grade rAAV vectors have largely been made in production systems that utilize transfection as a means of delivering the genetic elements needed for rAAV production in a cell. For example, removal of contaminating adenovirus helper has been circumvented by replacing adenovirus infection with plasmid transfection in a three-plasmid transfection system in which a third plasmid comprises nucleic acid sequences encoding adenovirus helper proteins (Xiao et al. 1998), Improvements in two-plasmid transfection systems have also simplified the production process and increased rAAV vector production efficiency (Grimm et al., 1998). Despite these advances, it is generally recognized that transfection systems are limited in their efficiency by the uptake of exogenous DNA, and in their commercial utility due to scaling difficulties.

Several strategies for improving yields of rAAV from cultured mammalian cells are based on the development of specialized producer cells created by genetic engineering. In one approach, production of rAAV on a large scale has been accomplished by using genetically engineered "proviral" cell lines in which an inserted AAV genome can be "rescued" by infecting the cell with helper adenovirus or HSV. Proviral cell lines can be rescued by simple adenovirus infection, offering increased efficiency relative to transfection protocols. However, as with the earlier transfection methods, adenovirus is introduced into the system that must later be removed. Additionally, the rAAV yield is generally low in proviral cell lines (Qiao et al. 2002a). There are several further disadvantages that limit approaches using proviral cell lines. The cell cloning and selection process itself can be laborious; additionally, this process must be carried out to generate a unique cell line for each therapeutic gene of interest (GOI). Furthermore, cell clones having inserts of unpredictable stability can be generated from proviral cell lines.

A second cell-based approach to improving yields of rAAV from cells involves the use of genetically engineered "packaging" cell lines that harbor in their genomes either the AAV rep and cap genes, or both the rep-cap and the ITR-gene of interest (Qiao et al., 2002b). In the former approach, in order to produce rAAV, a packaging cell line is either infected or transfected with helper functions, and with the AAV ITR-GOI elements. The latter approach entails infection or transfection of the cells with only the helper functions. Typically, rAAV production using a packaging cell line is initiated by infecting the cells with wild-type adenovirus, or recombinant adenovirus. Because the packaging cells comprise the rep and cap genes, it is not necessary to supply these elements exogenously.

While rAAV yields from packaging cell lines have been shown to be higher than those obtained by proviral cell line rescue or transfection protocols, packaging cell lines typically suffer from recombination events, such as recombination of E1a-deleted adenovirus vector with host 293 cell DNA. Infection with recombinant adenovirus therefore initiates both rAAV production and generation of replication-competent adenovirus. Furthermore, only limited success has been achieved in creating packaging cell lines with stable genetic inserts.

Recent progress in improving yields of rAAV has also been made using approaches based on delivery of helper functions from herpes simplex virus (HSV) using recombinant HSV amplicon systems. Although modest levels of rAAV vector yield, of the order of 150-500 viral genomes (vg) per cell, were initially repotted (Conway et al., 1997), more recent improvements in rHSV amplicon-based systems have provided substantially higher yields of rAAV v.g. and infectious particles (ip) per cell (Feudner et al., 2002). Amplicon systems are inherently replication-deficient; however the use of a "gutted" vector, replication-competent (rcHSV), or replication-deficient rHSV still introduces immunogenic HSV components into rAAV production systems. Therefore, appropriate assays for these components and corresponding purification protocols for their removal must be implemented. Additionally, amplicon stocks are difficult to generate in high titer, and often contain substantial parental virus contamination.

It is apparent from the foregoing that there is a clear need for improved large-scale methods for production of high titer, rAAV to overcome the major barrier to the routine use of rAAV for gene therapy. The current invention provides methods for producing clinically relevant recombinant AAV viral particles using mammalian cells capable of growing in suspension.

Methods of the Invention

Various embodiments of the present invention involve methods for producing recombinant AAV viral particles in a mammalian cell. The methods as described comprise in certain embodiments co-infecting a mammalian cell capable of growing in suspension with a first recombinant herpesvirus comprising a nucleic acid sequence encoding an AAV rep and an AAV cap gene each operably linked to a promoter, and a second recombinant herpesvirus comprising a gene of interest, and a promoter operably linked to said gene of interest, flanked by AAV inverted terminal repeats to facilitate packaging of the gene of interest, and allowing the virus to infect the mammalian cell, thereby producing recombinant AAV viral particles in a mammalian cell.

Any type of mammalian cell that is capable of supporting replication of herpesvirus is suitable for use according to the methods of the invention as described herein. Accordingly, the mammalian cell can be considered a host cell for the replication of herpesvirus as described in the methods herein. Any cell type for use as a host cell is contemplated by the present invention, as long as the cell is capable of supporting replication of herpesvirus. Examples of suitable genetically unmodified mammalian cells include but are not limited to cell lines such as HEK-293 (293), Vero, RD, BHK-21, HT-1080, A549, Cos-7, ARPE-19, and MRC-5. One of skill in the art would be familiar with the wide range of host cells that are available for use in methods for producing an rAAV, in particular examples a rAAV as described in the embodiments herein.

The host cells used in the various embodiments of the present invention may be derived, for example, from mammalian cells such as human embryonic kidney cells or primate cells. Other cell types might include, but are not limited to BHK cells, Vero cells, CHO cells or any eukaryotic cells for which tissue culture techniques are established as long as the cells are herpesvirus permissive. The term "herpesvirus permissive" means that the herpesvirus or herpesvirus vector is able to complete the entire intracellular virus life cycle within the cellular environment. In certain embodiments, methods as described occur in the mammalian cell line BHK, growing in suspension.

The host cell may be derived from an existing cell line, e.g., from a BHK cell line, or developed de novo.

U.S. Application No. 20070172846, incorporated by reference in its entirety herein, describes methodologies that have been used to adapt 293 cells into suspension cultures. Graham adapted 293A cells into suspension culture (293N3S cells) by 3 serial passages in nude mice (Graham, J. Gen. Virol., 68(Pt 3):937-940, 1987). The suspension 293N3S cells were found to be capable of supporting the replication of E1-deleted adenoviral vectors. However, Garnier et al. (Garnier et al., Cytotechnology, 15(1-3):145-155, 1994) observed that the 293N35 cells had a relatively long initial lag phase in suspension, a low growth rate, and a strong tendency to clump.

A second method that has been used is a gradual adaptation of 293A cells into suspension growth (Cold Spring Harbor Laboratories, 293S cells). Garnier et al. (1994) reported the use of 293 S cells for production of recombinant proteins from adenoviral vectors. The authors found that 293S cells were much less clumpy in calcium-free media and a fresh medium exchange at the time of virus infection could significantly increase the protein production. It was found that glucose was the limiting factor in culture without medium exchange.

The methods of the invention include also a recombinant AAV viral particle produced in a mammalian cell by the method comprising co-infecting a mammalian cell capable of growing in suspension with a first recombinant herpesvirus comprising a nucleic acid encoding an AAV rep and an AAV cap gene each operably linked to a promoter; and (ii) a second recombinant herpesvirus comprising a gene of interest, and a promoter operably linked to said gene of interest; and allowing the virus to infect the mammalian cell, and thereby producing recombinant AAV viral particles in a mammalian cell. As described herein, the herpesvirus is a virus selected from the group consisting of: cytomegalovirus (CMV), herpes simplex (HSV) and varicella zoster (VZV) and epstein barr virus (EBV). The recombinant herpesvirus is replication defective. The AAV cap gene has a serotype selected from the group consisting of AAV-1, AAV-2, AAV-3, AAV-4, AAV-5, AAV-6, AAV-7, AAV-8, AAV-9, and rhAAV-10.

As described in greater detail in other parts of the application, the recombinant viral particle described herein, wherein the gene of interest is a therapeutic gene, that can be, but is in no way limited to, a gene is selected from the group consisting of; anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc finger, nucleic acid binding protein (known as CNBP or ZNF9), Retinitis pigmentosa GTPase regulator (RPGR), Acid α-glucosidase (GAA), Choroideremia (CHM), Rab escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase.

Diseases to be Treated

In embodiments of the instant invention where the method for producing recombinant AAV viral particles in a mammalian cell comprises co-infecting a mammalian cell capable of growing in suspension with a first recombinant herpesvirus and a second recombinant herpesvirus comprising a gene of interest, the invention contemplates use of any gene that has therapeutic or potential therapeutic value in the treatment of a disease or genetic disorder. One of skill in the art would be familiar with the wide range of such genes that have been identified.

In certain embodiments, the therapeutic genes involved may be those that encode proteins, structural or enzymatic RNAs, inhibitory products such as antisense RNA or DNA, or any other gene product. Expression is the generation of such a gene product or the resultant effects of the generation of such a gene product. Thus, enhanced expression includes the greater production of any therapeutic gene or the augmentation of that product's role in determining the condition of the cell, tissue, organ, or organism.

In certain embodiments, the therapeutic gene may encode one or more anti-angiogenic proteins.

For example, the therapeutic gene can be, but is not limited to an antisense gene, for example antisense ras, antisense myc, antisense raf, antisense erb, antisense src, antisense fms, antisense jun, antisense trk, antisense ret, antisense gsp, antisense hst, antisense bcl, antisense abl, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus-1, interferon .alpha., interferon .beta., interferon .gamma., ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NTS, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, Ep1A, p300, VEGF, FGF, thrombospondin, BAI-1, GDAIF, or MCC. In further embodiments of the present invention, the recombinant gene is a gene encoding an ACP desaturase, an ACP hydroxylase, an ADP-glucose pyrophorylase, an ATPase, an alcohol dehydrogenase, an alpha 1 antitrypsin gene, an amylase, an amyloglucosidase, a catalase, a cellulase, a cyclooxygenase, a decarboxylase, a dextrinase, an esterase, a DNA polymerase, an RNA polymerase, FLt01, a hyalnron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine. In other embodiments of the present invention, the recombinant gene is a gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione .beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta.-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, .alpha.-L-iduronidase, glucose-6-phosphate dehydrogenase, HSV thymidine kinase, or human thymidine kinase. Alternatively, the recombinant gene may encode growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, beta.-endorphin, .beta.-melanocyte stimulating hormone, cholecystokinin, endothelin I, galanin, gastric inhibitory peptide, glucagon, insulin, lipotropins, neurophysins, somatostatin, calcitonin, calcitonin gene related peptide, beta-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

In other embodiments, the therapeutic gene of the invention is anti-angiogenic genes, alpha-1 antitrypsin, retinoschisin, acid alpha glucosidase, RPE65, beta-subunit of the cone photoreceptor cGMP-gated channel (CNGB-3), alpha-subunit of the cone photoreceptor cGMP-gated channel (CNGA-3), cone photoreceptor G-protein alpha-subunit (GNAT2), Retinal pigment epithelium-specific 65 kDa (RPE65), X-linked juvenile retinoschisis (RS1), Brain-derived neurotrophic factor (BDNF), Glial cell-derived neurotrophic factor (GDNF), Myotonic dystrophy protein kinase (DMPK), CCHC-type zinc linger, nucleic acid binding protein (known as CNBP or ZNF9), Retinitis pigmentosa GTPase regulator (RPGR), Acid α-glucosidase (GAA), Choroideremia (CHM), Rab escort protein-1 (REP1), Alpha-synuclein (SNCA), Coagulation factor VIII, procoagulant component (hemophilia A or F8), Coagulation factor IX (plasma thromboplastic component, Christmas disease, hemophilia B or F9), Aryl hydrocarbon receptor interacting protein-like 1 (AIPL1), X-linked Inhibitor of Apoptosis Protein (XIAP), clarin-1 (CLRN1), Leber's hereditary neuropathy genes (MT-ND1, MT-ND4, MT-ND4L, and MT-ND6), alpha-galactosidase A (α-Gal A) or Alpha-L-iduronidase. In certain preferred embodiments of the invention, the therapeutic gene of interest is an angiogenesis inhibition gene (AI) or an alpha 1 antitrypsin gene (AAT).

Production Technologies for rAAV

U.S. application Ser. No. 11/503,775, incorporated by reference in its entirety herein, describes required elements of rAAV Production Systems. Recombinant AAV is produced in vitro by introduction of gene constructs into cells known as producer cells. Known systems for production of rAAV employ three fundamental elements: 1) a gene cassette containing the gene of interest, 2) a gene cassette containing AAV rep and cap genes and 3) a source of "helper" virus proteins.

The first gene cassette is constructed with the gene of interest flanked by inverted terminal repeats (ITRs) from AAV. ITRs function to direct integration of the gene of interest into the host cell genome and are essential for encapsidation of the recombinant genome. (Hermonat and Muzyczka, 1984, Samulski, et. al., 1983). The second gene cassette contains rep and cap, AAV genes encoding proteins needed for replication and packaging of rAAV. The rep gene encodes four proteins (Rep 78, 68, 52 and 40) required for DNA replication. The cap genes encode three structural proteins (VP1, VP2, and VP3) that make up the virus capsid (Muzyczka and Berns, 2001.)

The third element is required because AAV does not replicate on its own. Helper functions are protein products from helper DNA viruses that create a cellular environment conducive to efficient replication and packaging of rAAV. Traditionally, adenovirus (Ad) has been used to provide helper functions for rAAV, but herpesviruses can also provide these functions as discussed below.

Production of rAAV vectors for gene therapy is carried out in vitro, using suitable producer cell lines such as BHK cells grown in suspension. Other cell lines suitable for use in the invention include HEK-293 (293), Vero, RD, BHK-21, HT-1080, A549, Cos-7, ARPE-19, and MRC-5.

Any cell type can be used as a host cell, as long as the cell is capable of supporting replication of a herpesvirus. One of skill in the art would be familiar with the wide range of host cells that can be used in the production of herpesvirus from host cells. Examples of suitable genetically unmodified mammalian host cells, for example, may include but are not limited to cell lines such as HEK-293 (293), Vero, RD, BHK-21, HT-1080, A549, Cos-7, ARPE-19, and MRC-5.

In particular embodiments, a host cell is adapted for growth in suspension culture. In certain embodiments of the present invention, the host cells are Baby Hamster Kidney (BHK) cells. BHK cell line grown in suspension is derived from an adaptation of the adherent BHK cell line. Both cell lines are available commercially.

A well known strategy for delivering all of the required elements for rAAV production utilizes two plasmids and a helper virus. This method relies on transfection of the producer cells with plasmids containing gene cassettes encoding the necessary gene products, as well as infection of the cells with Ad to provide the helper functions. This system employs plasmids with two different gene cassettes. The first is a proviral plasmid encoding the recombinant DNA to be packaged as rAAV. The second is a plasmid encoding the rep and cap genes, To introduce these various elements into the cells, the cells are infected with Ad as well as transfected with the two plasmids. The gene products provided by Ad are encoded by the genes E1a, E1b, E2a, E4orf6, and Va (Samulski et al., 1998: Hauswirth et al., 2000; Muzyczka and Burns, 2001). Alternatively, in more recent protocols, the Ad infection step can be replaced by transfection with an adenovirus "helper plasmid" containing the VA, E2A and E4 genes (Xiao, et al., 1998, Matsushita, et al, 1998).

While Ad has been used conventionally as the helper virus for rAAV production, it is known that other DNA viruses, such as herpes simplex virus type 1 (HSV-1) can be used as well. The minimal set of HSV-1 genes required for AAV2 replication and packaging has been identified, and includes the early genes UL5, UL8, UL52 and UL29 (Muzyczka and Burns, 2001). These genes encode components of the HSV-1 core replication machinery, i.e., the helicase, primase, primase accessory proteins, and the single-stranded DNA binding protein (Knipe, 1989; Weller, 1991). This rAAV helper property of HSV-1 has been utilized in the design and construction of a recombinant herpes virus vector capable of providing helper virus gene products needed for rAAV production (Conway et al., 1999).

Production of rAAV vectors for gene therapy is carried out in vitro, using suitable producer cell lines such as BHK cells grown in suspension. Other cell lines suitable for use in the invention include HEK-293 (293), Vero, RD, BHK-21, HT-1080, A549, Cos-7, ARPE-19, and MRC-5.

Any cell type can be used as a host cell, as long as the cell is capable of supporting replication of a herpesvirus. One of skill in the art would be familiar with the wide range of host-cells that can be used in the production of herpesvirus from host cells. Examples of suitable genetically unmodified mammalian host cells, for example, may include but are not limited to cell lines such as HEK-293 (293), Vero, RD, BHK-21, HT-1080, A549, Cos-7, ARPE-19, and MRC-5.

In particular embodiments, a host cell is adapted for growth in suspension culture. In certain embodiments of the present invention, the host cells are Baby Hamster Kidney (BHK) cells. BHK cell line grown in suspension is derived from an adaptation of the adherent BHK cell line. Both cell lines are available commercially.

rHSV-Based rAAV Manufacturing Process

The instant invention provides production of recombinant AAV viral particles in cells growing in suspension. Suspension or non-anchorage dependent cultures from continuous established cell lines are the most widely used means of large scale production of cells and cell products. Large scale suspension culture based on fermentation technology has clear advantages for the manufacturing of mammalian cell products. The processes are relatively simple to operate and straightforward to scale up. Homogeneous conditions can be provided in the bioreactor which allows for precise monitoring and control of temperature, dissolved oxygen, and pH, and ensure that representative samples of the culture can be taken. The rHSV vectors used are readily propagated to high titer on permissive cell lines both in tissue culture flasks and bioreactors, and provided a production protocol amenable to scale-up for virus production levels necessary for clinical and market production.

Cell culture in stirred tank bioreactors provides very high volume-specific culture surface area and has been used for the production of viral vaccines (Griffiths, 1986). Furthermore, stirred tank bioreactors have industrially been proven to be scalable. One example is the multiplate CELL CUBE cell culture system. The ability to produce infectious viral vectors is increasingly important to the pharmaceutical industry, especially in the context of gene therapy.

As used herein, a "bioreactor" refers to any apparatus that can be used for the purpose of culturing cells. Growing cells according to the present invention in a bioreactor allows for large scale production of fully biologically-active cells capable of being infected by the Herpes vectors of the present invention.

Bioreactors have been widely used for the production of biological products from both suspension and anchorage dependent animal cell cultures. Most large-scale suspension cultures are operated as batch or fed-batch processes because they are the most straightforward to operate and scale up. However, continuous processes based on chemostat or perfusion principles are available.

The bioreactor system can, in certain embodiments, be set up to include a system to allow for media exchange. For example, filters may be incorporated into the bioreactor system to allow for separation of cells from spent media to facilitate media exchange. In some embodiments of the present methods for producing Herpes virus, media exchange and perfusion is conducted beginning on a certain day of cell growth. For example, media exchange and perfusion can begin on day 3 of cell growth. The filter may be external to the bioreactor, or internal to the bioreactor.

EXAMPLES

It should be appreciated that the invention should not be construed to be limited to the examples that are now described; rather, the invention should be construed to include any and all applications provided herein and all equivalent variations within the skill of the ordinary artisan.

Example 1: Materials and Methods of the Invention

The invention was performed using the following methods. The methods as described herein are described in PCT application No. PCT/US2007/017645, filed on Aug. 8, 2007, entitled Recombinant AAV Production in Mammalian Cells, which claims the benefit of U.S. application Ser. No. 11/503,775, entitled Recombinant AAV Production in Mammalian Cells, filed Aug. 14, 2007, which is a continuation-in-part of U.S. application Ser. No. 10/252,182, entitled High Titer Recombinant AAV Production, filed Sep. 23, 2002, now U.S. Pat. No. 7,091,029, issued Aug. 15, 2006. The contents of all the aforementioned applications are hereby incorporated by reference in their entirety.

rHSV Co-Infection Method

The rHSV co-infection method for recombinant adeno-associated virus (rAAV) production employs two ICP27-deficient recombinant herpes simplex virus type 1 (rHSV-1) vectors, one bearing the AAV rep and cap genes (rHSV-rep2capX, with "capX" referring to any of the AAV serotypes), and the second bearing the gene of interest (GOI) cassette flanked by AAV inverted terminal repeats (ITRs). Although the system was developed with AAV serotype 2 rep, cap, and ITRs, as well as the humanized green fluorescent protein gene (GFP) as the transgene, the system can be employed with different transgenes and serotype/pseudotype elements.

Mammalian cells are infected with the rHSV vectors, providing all cis and trans-acting rAAV components as well as the requisite helper functions for productive rAAV infection. Cells are infected with a mixture of rHSV-rep2capX and rHSV-GOI. Cells are harvested and lysed to liberate rAAV-GOI, and the resulting vector stock is titered by the various methods described below.

DOC-Lysis

At harvest, cells and media are separated by centrifugation. The media is set aside while the cell pellet is extracted with lysis buffer (20 mM Tris-HCl, pH 8.0, 150 mM NaCl) containing 0.5% (w/v) deoxycholate (DOC) using 2 to 3 freeze-thaw cycles, which extracts cell-associated rAAV. In some instances, the media and cell-associated rAAV lysate is recombined.

In Situ Lysis

An alternative method for harvesting rAAV is by in situ lysis. At the time of harvest, $MgCl_2$ is added to a final concentration of 1 mM, 10% (v/v) Triton X-100 added to a final concentration of 1% (v/v), and Benzonase is added to a final concentration of 50 units/mL. This mixture is either shaken or stirred at 37° C. for 2 hours.

Quantitative Real-Time PCR to Determine DRP Yield

The DNAse-resistant particle (DRP) assay employs sequence-specific oligonucleotide primers and a dual-labeled hybridizing probe for detection and quantification of the amplified DNA sequence using real-time quantitative polymerase chain reaction (qPCR) technology. The target sequence is amplified in the presence of a fluorogenic probe which hybridizes to the DNA and emits a copy-dependent fluorescence. The DRP titer (DRP/mL) is calculated by direct comparison of relative fluorescence units (RFUs) of the test article to the fluorescent signal generated from known plasmid dilutions bearing the same DNA sequence. The data generated from this assay reflect the quantity of packaged viral DNA sequences, and are not indicative of sequence integrity or particle infectivity.

Green-Cell Infectivity Assay to Determine Infectious Particle Yield (rAAV-GFP Only)

Infectious particle (ip) titering is performed on stocks of rAAV-GFP using a green cell assay. C12 cells (a HeLa derived line that expressed AAV2 Rep and Cap genes—see references below) are infected with serial dilutions of rAAV-GFP plus saturating concentrations of adenovirus (to provide helper functions for AAV replication). After two to three days incubation, the number of fluorescing green cells (each cell representing one infectious event) are counted and used to calculate the ip/mL titer of the virus sample.

Clark K R et al. described recombinant adenoviral production in Hum. Gene Ther. 1995. 6:1329-1341 and Gene Ther. 1996. 3:1124-1132, both of which are incorporated by reference in their entireties herein.

$TCID_{50}$ to Determine rAAV Infectivity

Infectivity of rAAV particles harboring a gene of interest (rAAV-GOI) was determined using a tissue culture infectious dose at 50% ($TCID_{50}$) assay. Eight replicates of rAAV were serially diluted in the presence of human adenovirus type 5 and used to infect HeLaRC32 cells (a HeLa-derived cell line that expresses AAV2 rep and cap, purchased from ATCC) in a 96-well plate. At three days post-infection, lysis buffer (final concentrations of 1 mM Tris-HCl pH 8.0, 1 mM EDTA, 0.25% (w/v) deoxycholate, 0.45% (v/v) Tween-20, 0.1% (w/v) sodium dodecyl sulfate, 0.3 mg/mL Proteinase K) was added to each well then incubated at 37° C. for 1 h, 55° C. for 2 h, and 95° C. for 30 min. The lysate from each well (2.5 µL aliquot) was assayed in the DRP qPCR assay described above. Wells with Ct values lower than the value of the lowest quantity of plasmid of the standard curve were scored as positive. $TCID_{50}$ infectivity per mL ($TCID_{50}$/mL) was calculated based on the Kärber equation using the ratios of positive wells at 10-fold serial dilutions.

Cell Lines and Viruses

Production of rAAV vectors for gene therapy is carried out in vitro, using suitable producer cell lines such as BHK cells grown in suspension. Other cell lines suitable for use in the invention include HEK-293 (293), Vero, RD, BHK-21, HT-1080, A549, Cos-7, ARPE-19, and MRC-5.

Mammalian cell lines were maintained in Dulbecco's modified Eagle's medium (DMEM, Hyclone) containing 2-10% (v/v) fetal bovine serum (FBS, Hyclone) unless otherwise noted. Cell culture and virus propagation were performed at 37° C., 5% CO2 for the indicated intervals.

Cell Seeding Density

Host cell suspension stocks, such as BHK suspension cell stock, may be used to seed spinner flasks, shaker flasks, bioreactors or other cultures at various seeding densities. Satisfactory cell growth may be achieved with a wide range of cell seeding densities. For optimal cell growth the cell seeding density is recommended to be at least about, at most about, about, or higher than $2 \times 10^5$ cells/mL and includes, but is not limited to cell densities of at least about, at most about, or about $5 \times 10^5$ cells/mL, including all values or ranges there between.

Culture Temperature

Cells can be cultured at temperatures that include, but are not limited to at least about, at most about, or about 32.degree. C., 33.degree. C., 34.degree. C., 35.degree. C., 36.degree. C., 37.degree. C., 38.degree., C., 39.degree. C. or 40.degree. C., including all values therebetween. In certain aspects of the invention the incubation temperature for growth of BHK suspension cells will be 37 degree C.

$CO_2$ Percentage

Cells may be cultured in spinner flasks inside incubators or in bioreactors having an atmosphere of at least about, at most about, or about 0, 5, 10, 15, or 20% CO2. In certain preferred embodiments, cell growth was achieved at CO2 percentages of 5% CO2. Typically, the growth of suspension cells requires CO2 in the culture environment and should be maintained between 4 and 6 percent or any value or range there between.

Cell Growth in Spinner Flask or Bioreactor

In certain embodiments, a spinner flask may be used and seeded with suspension cells at an appropriate cell seeding density as described herein. In other certain embodiments, a bioreactor may be used such as a Wave disposable bioreactor or a continuous stirred-tank bioreactor) and seeded with suspension cells at an appropriate cell seeding density. Cells are grown inside the spinner flask or bioreactor.

When cells reach a density between $9 \times 10^5$ and $2.5 \times 10^6$ cells/mL, nutrients can be replenished and waste byproducts removed by media exchange, dilution, or perfusion (continuous media input and removal). Alternatively, the cells can be kept at the higher density to grow cells to the density desired for rAAV production, in either a spinner flask or bioreactor. Accordingly, a high cell concentration is expected, in certain preferred embodiments, to improve the volumetric productivity of recombinant AAV production.

The bioreactor can hold any volume of media, for example a 10 L Wave bioreactor can hold up to 5 L working volume). In certain embodiments, the bioreactor can be adjusted to rock at a particular speed and angle. In certain other embodiments, the bioreactor may include a device for monitoring dissolved oxygen tension, such as a disposable dissolved oxygen tension (DOT) probe. The bioreactor may also include a device for monitoring temperature in the media. Other embodiments include a device for measuring and adjusting culture pH, such as a gas mixer which can adjust CO.sub.2 gas percentage delivered to the media. The bioreactor may or may not be a disposable bioreactor.

Multiplicity of Infection (MOI)

Cells can be infected with recombinant herpesviruses at a combined MOI of between 3 and 14 plaque forming units per cell (pfu/cell). A relatively consistent virus yield is observed with a combined MOI at or above 6 pfu/cell. Data suggest that combined MOIs between 6 and 14 pfu/cell appear to be the optimal range for rAAV production in BHK suspension culture.

In preferred embodiments, the invention requires co-infection of cells with a replication-deficient rHSV vector that provides helper functions for rAAV production. The invention provides a simplified rHSV-based system for rAAV production that uses two or more replication-deficient rHSV vectors including one for the delivery of the rAAV rep and cap functionalities and one for delivery of the therapeutic gene (the gene of interest). Advantageously, the availability of separate replication-defective rHSV vectors of the invention as described makes it possible to modulate the rep and cap functionalities relative to the gene of interest, by varying the co-infection MOI. The optimal ratio is 2:1, but rAAV production can occur with ratios of 1:2 to 6:1 of rHSV-rep2capX and rHSV-GOI, respectively, Infection Cell Density Cells can be grown to various concentrations including, but not limited to at least about, at most about, or about $1 \times 10^6$ to $4 \times 10^6$ cells/mL. The cells can then be infected with recombinant herpesvirus at a predetermined MOI.

Media Nutrient Level

In certain embodiments of the invention, the conditions of infection comprise media exchange on or about, but not limited to 2 hours post-infection. Fresh media is preferably, but not limited to, Dulbecco's modified Eagle's medium (DMEM, Hyclone) lacking FBS.

rHSV-1 Vector Construction and Production

A rHSV-rep2cap2 (originally denoted d27.1-rc) was constructed as previously described. Briefly, rHSV-rep2cap2 was constructed by homologous recombination of an AAV2 rep and cap gene cassette into the tk locus of the rHSV-1, ICP27-deleted d27.1 vector in which the AAV2 rep and cap genes are under control of their native promoters (p5, p19 and p40). The rHSV-rep2cap1 vector was constructed by as described above using cap1. In this method, any combination of rep and cap can be used.

The rHSV-AAV2/GFP vector (referred to as rHSV-GFP) was constructed by homologous recombination of a CMV promoter-driven hGFP-neomycin resistance gene cassette, flanked by the AAV2 ITRs, into the tk locus of the d27.1 vector as described above.

In certain embodiments, it may be useful to employ selection systems that preclude growth of undesirable cells. This may be accomplished by virtue of permanently transforming a cell line with a selectable marker or by transducing or infecting a cell line with a viral vector that encodes a selectable marker. In either situation, culture of the transformed/transduced cell with an appropriate drug or selective compound will result in the enhancement, in the cell population, of those cells carrying the marker.

The rHSV-rep2capX and rHSV-GOI vectors were propagated on the ICP27-complementing cell line V27. V27 is an ICP27-expressing Vero cell line derivative which harbors approximately one copy of the ICP27 gene per haploid genome equivalent. Infection steps were done in the absence of serum. Vector stocks were propagated either by seeding T225 flasks with $3\times10^7$ V27 cells, or 10-stack cell factories with $1.5\times10^9$ V27 cells, followed by infecting 24 h post-seeding with either rHSV-rep2capX or rHSV-GOI at a MOI of 0.15. rHSV vectors were harvested at 72 hours post-infection (h.p.i.) by separating the infected cells from the media centrifugation (10 min, 4° C., 1100 g). The supernatant is set aside while the cell pellet is treated with 0.6 M NaCl in 1× Phosphate-buffered saline, pH 6.5, for 30 minutes at 37° C., The cells are then re-pelleted by centrifugation as above. This second supernatant is recombined with the first supernatant (with the cell pellet discarded), formulated with 5% (v/v) sterile glycerol and was stored at $-80°$ C., rHSV-1 vector stocks were used for rAAV production without further manipulation.

Example 2: Suspension BHK (sBHK) Cell Propagation and Characterization, and Production of rAAV2 in Suspension BHK Cells rAAV Production in Two Clones of sBHK Numerous cell lines are capable of producing high specific yields of recombinant adeno-associated virus (rAAV) vectors using the rHSV co-infection method, as described in U.S. application Ser. No. 11/503,775, which is a continuation-in-part of U.S. application Ser. No. 10/252,182, now U.S. Pat. No. 7,091,029, issued Aug. 15, 2006, both of which are incorporated by reference herein. Baby hamster kidney cells clone 13 (BHK-21) and human embryonic kidney cells (HEK 293) produce the highest levels of rAAV particularly in comparison to traditional methods of rAAV production (as described in U.S. application Ser. No. 11/503,775, above). Large quantities of recombinant AAV vector are required for clinical application, however, the adherent nature of these cells is an impediment to large scale production. Therefore, cells that grow in suspension offer an economic and process advantage for rAAV production. In this example, two independent isolates of BHK-21 cells selected to grow in suspension were analyzed for rAAV production using the rHSV co-infection method. Cells were cultured in spinner flasks according to recommended guidelines (maintenance between $2\times10^5$ and $1.3\times10^6$ cells/mL) and were co-infected with rHSV-rep2cap2 and rHSV-GFP at a multiplicity of infection (MOI) of 12 and 2. Starting 24 hours post infection (hpi), samples of the infected cultures were taken at 24 hour intervals. Cells were processed using the DOC-lysis method (see Methods). Specific yields of infectious particles (ip) per cell (ip/cell) were determined by the green-cell infectivity assay. The combined yield of cell-associated and released (media) rAAV2-GFP for each suspension BHK (sBHK) isolate at each time point is presented in FIG. 1. The C13-2P and AC9 isolates produced rAAV levels similar to previously examined adherent cell lines with 3800 and 1200 ip/cell by 48 hpi, respectively, described in U.S. application Ser. No. 11/503,775, entitled Recombinant AAV Production in Mammalian Cells, filed Aug. 14, 2007, which is a continuation-in-part of U.S. application Ser. No. 10/252,182, entitled High Titer Recombinant AAV Production, filed Sep. 23, 2002, now U.S. Pat. No. 7,091,029, issued Aug. 15, 2006, both of which are incorporated by reference in their entireties herein.

Growth of Suspension BHK Cells

Clone C13-2P (referred to from this point on as "sBHK") was selected for additional experiments due to the higher level of rAAV production. The growth of these cells was further characterized. The cells are maintained between $2\times10^5$ and $1.3\times10^6$ cells/mL in DMEM supplemented with 10% FBS. Numerous vials of sBHK cells have been thawed. Specifically, 33 vials representing 6 banks of cells have been thawed and propagated with a mean doubling time of 11.9+/−1.9 hours (a variance of 16.3%). In comparison, adherent 293 cells have a doubling time of ~22-24 hours. Therefore, the faster doubling of the sBHK cells provides the advantage of faster amplification for scale-up.

Example 3. rAAV Production Over Time

Figure 2:
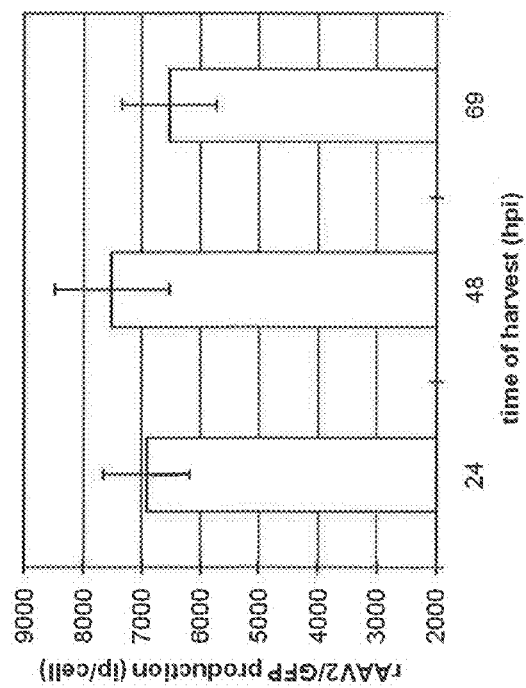
FIG. 2 is a graph that shows rAAV production over time. Cells were co-infected at $1.0 \times 10^6$ cells/mL with rHSV-rep2cap2 and rHSV-GFP at an MOI of 12 and 2, respectively. Two hours post-infection, cells were pelleted and re-suspended in DMEM without FBS. Samples of the production over time were assayed for the level of rAAV2-GFP production by the green-cell infectivity assay. Error bars represent the standard deviation over 3 flasks.

The optimal harvest time of rAAV production in adherent 293 cells is 48-72 hpi. Due to the faster growth rate of the sBHK cells, we wanted to re-examine the optimal time range for rAAV production in the suspension platform. The experiment shown in FIG. 2 demonstrated that rAAV production levels are similar when harvested between 24 and 69 hours post-infection (hpi). The ability to achieve similar rAAV yields at 24 hpi as at later times offers the advantages of shorter manufacturing times and flexibility in manufacturing schedules.

Example 4. Cell Density at Infection

Figure 3:
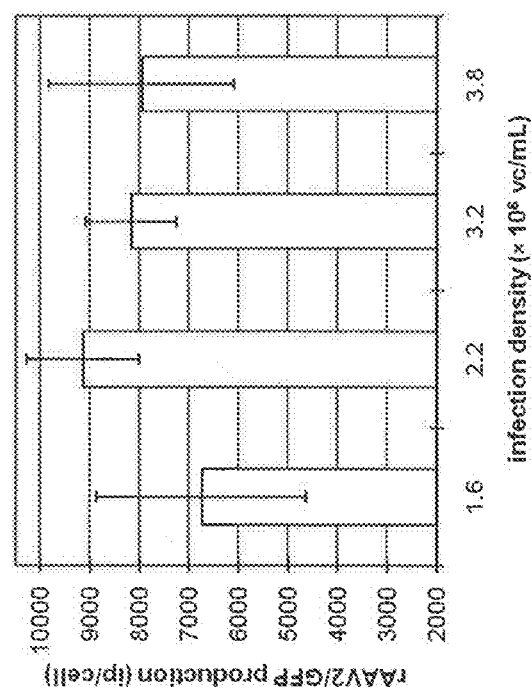
FIG. 3 is a graph that shows cell density at infection. sBHK cells at the range of cell densities indicated in a total volume of 25 ml were co-infected with rHSV-rep2cap2 and rHSV-GFP at an MOI of 12 and 2, respectively. Two hours post-infection, cells were pelleted and resuspended in DMEM without FBS. Samples were harvested by in situ lysis at 22 hpi and were assayed for the level of rAAV2-GFP production (ip/cell—bars; total ip in the 25 ml, culture—open circles) by the green-cell infectivity assay. Error bars represent the infra-assay variation.

Early experiments with sBHK examining rAAV production levels were performed with the cells infected at densities between $4.5\times10^5$ and $1\times10^6$ cells/mL—densities that fall within the range used for routine maintenance of the cells. However, we found that higher densities could easily be reached. This example addressed whether specific yields of rAAV could be maintained upon rHSV co-infection when the cells are at a higher density. Cell densities between $1.6\times10^6$ and $3.8\times10^6$ cells/mL, at a scale of 25 mL, were examined for rAAV production. The results in FIG. 3 demonstrated that increasing the sBHK cell density at the time of infection does not impair the specific yields (per cell yields) of rAAV. The volumetric productivity (DRP/L) is directly proportional to the sBHK cell density at constant specific yield, therefore total DRP/batch can be increased by increasing the cell density while minimizing the final volume required to achieve clinically relevant quantities of therapeutic vector.

Example 5. Multiplicity of Infection

Figure 4:
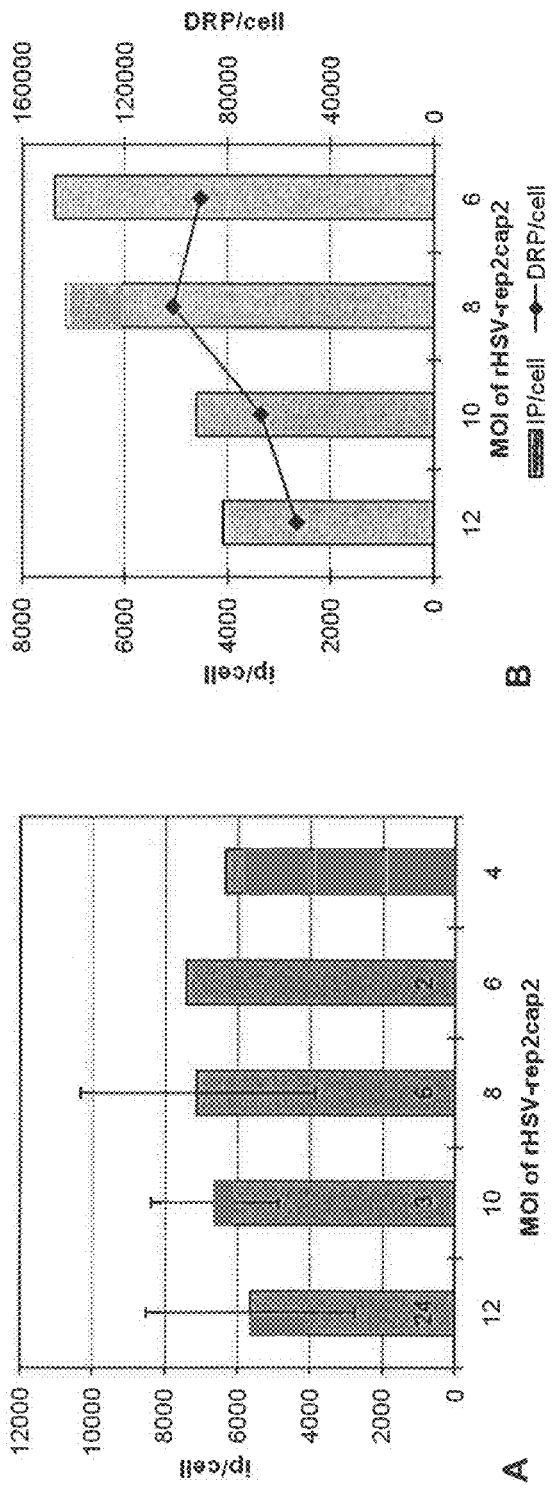
FIGS. 4 (A and B) is two graphs that show rAAV production over of range of MOI for rHSV-rep2cap2.

The rHSV co-infection method produces optimal levels of recombinant rAAV on adherent cells when rHSV-rep2capX and rHSV-GOI are used at MOIs of 12 and 2, respectively. The productions levels drop precipitously as the MOI of rHSV-rep2capX drops. Using an MOI of 12 for the rHSV-rep2capX translates into very large quantities of recombinant virus required when considering large scale manufacturing of rAAV. This example addressed whether the MOI of rHSV-rep2capX in co-infections on sBHK cells, unlike 293 cells, could be lowered without significant loss of specific yield. The results in FIG. 4 are the cumulative data of several experiments examining rAAV production levels when rHSV-rep2cap2 is used at an MOI of 4 to 12 (with rHSV-GOI MOI held constant at 2).

Figure 5:
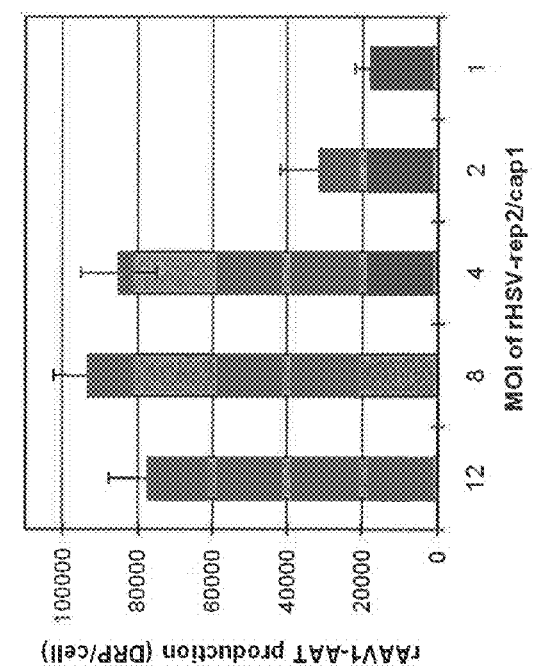
FIG. 5 is a graph that shows rAAV production over of range of MOI for rHSV-rep2cap1. Cumulative data for experiments examining rAAV production with rHSV-rep2cap1 used in co-infections over the indicated range of MOIs is presented. All co-infections were performed with rHSV-AAT used at an MOI of 2 and cells were infected at densities ranging from $1.45 \times 10^6$ to $2.40 \times 10^6$ cells/mL. Two hours post-infection, cells were pelleted and resuspended in DMEM without FBS. Samples were harvested by in situ lysis between 23 and 48 hpi and were assayed for the level of rAAV1-AAT production by the DNAse-resistant particle—quantitative real-time PCR. The numbers inside the bars represent the number of flasks assayed at the indicated MOI. Error bars represent inter-assay variation.

The results in FIG. 5 are the cumulative data of several experiments examining rAAV production levels when rHSV-rep2cap1 is used at an MOI of 1 to 12. rAAV1-AAT production in sBHK cells was also insensitive to rHSV-rep2/cap1 vector MOI inputs of 12, 8, and 4; however, rAAV1-AAT yields dropped according with further reductions in rHSV-AAT MOI to 2 and 1.

Taken together, these results demonstrate that comparable rAAV production can be achieved across a broad range of MOIs for rHSV-rep2capX.

Figure 6:
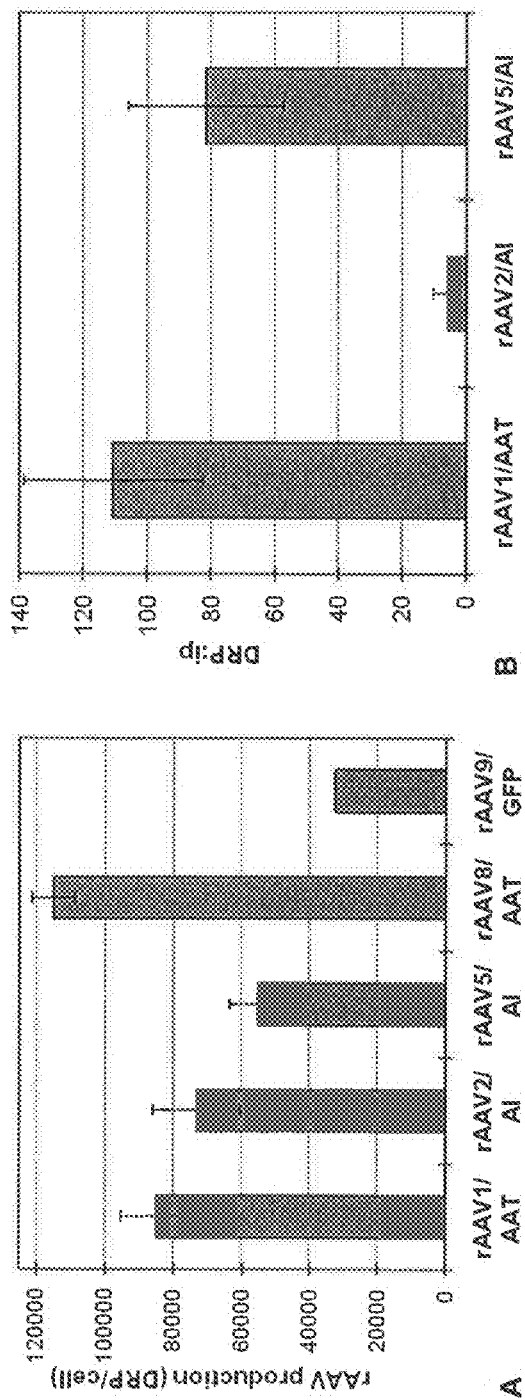
FIG. 6A is a graph that shows production levels of rAAV of different capsid serotypes (1, 2, 5, 8, and 9) with different trans genes (AI, AAT, and GFP). All co-infections were performed with rHSV-rep2capX at an MOI of 4 and rHSV-GOI at an MOI of 2 and cells were infected at densities ranging from $1.2 \times 10^6$ to $2.0 \times 10^6$ cells/mL. Two hours post-infection, cells were pelleted and resuspended in DMEM without FBS. Samples were harvested by in situ lysis between 24 and 30 hpi and were assayed for the level of rAAVX-GOI production by the DNAse-resistant particle—quantitative real-time PCR. Error bars represent inter-assay variation. Representative samples from the experiments in FIG. 6A were assayed for infectivity using the $TCID_{50}$ end-point dilution assay. The DRP/infectivity ratios (DRP:ip) are depicted in FIG. 6B. The differences in infectivity between the three serotypes indicated (rAAV types 1, 2, and 5), reflect the differences in these cell types in their ability to infect the HeLa-derived cells used in the infectivity assay.

Example 6. Applicability of System to Different rAAV Serotypes and Different Transgenes In certain embodiments of the invention a second recombinant herpesvirus comprises a gene of interest, and a promoter operably linked to said gene of interest. The gene of interest can be a therapeutic gene that is useful for gene therapy applications. This example demonstrates that the sBHK system for producing rAAV vectors can be used for a variety of AAV serotypes as well as different transgenics and production scales. FIG. 6A shows the yields of different serotypes and transgenes used in the sBHK system. FIG. 6B shows the DRP to infectivity ratios of representative samples from FIG. 6A. The differences between the serotypes reflect their in vitro infectivity variation on the cell-type used for the infectivity assay.

Example 7. Production of rAAV in Suspension BHK Cells in Bioreactors

Figure 7:
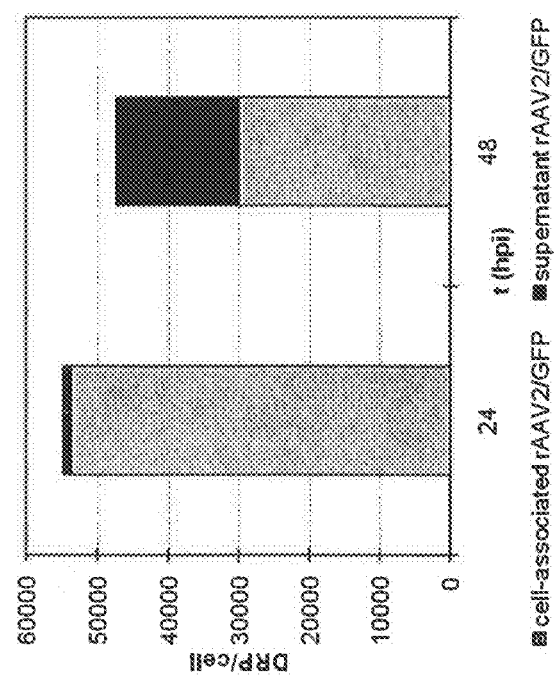
FIG. 7 is a graph that shows rAAV2-GFP production in a Celligen Plus CSTR. At 24 hpi, the DRP:ip was 10:1 and the capsid:DRP was 4.4:1 (cell-associated vector). During cell growth, the average doubling time was 9.6 h.
Figure 8:
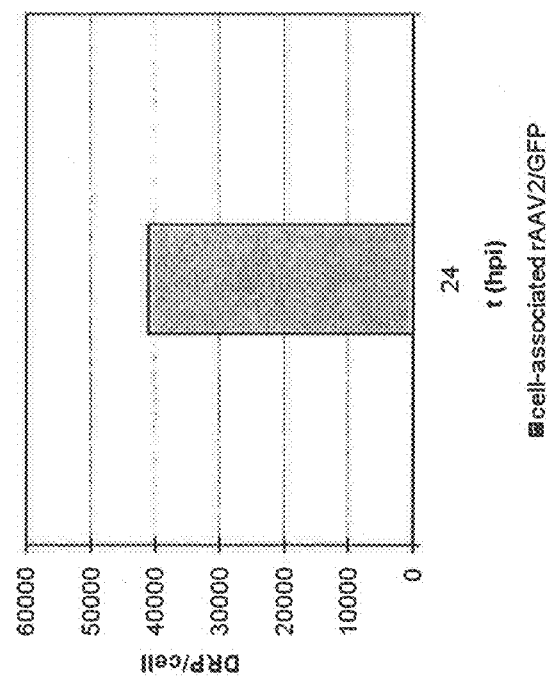
FIG. 8 is a graph that shows the results of an experiment that is a repeat of rAAV2-GFP production in a Celligen Plus CSTR as shown in FIG. 7. The DRP:ip was 11:1 and the capsid:DRP was 6.6:1 (cell-associated vector).
Figure 9:
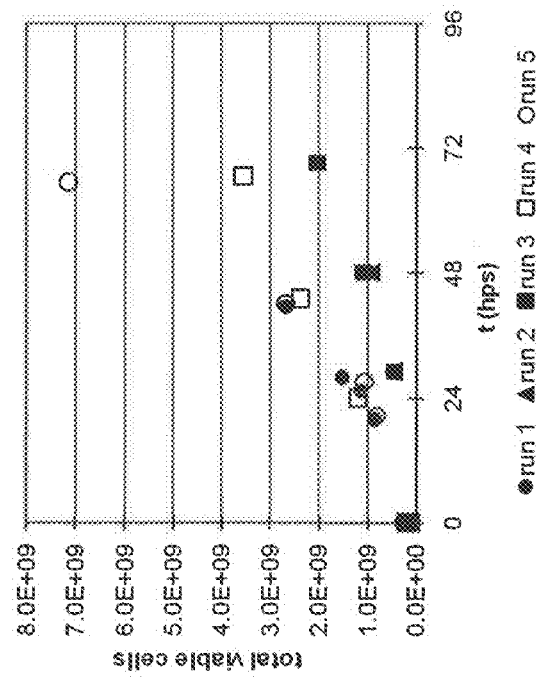
FIG. 9 is a graph that shows pre-infection sBHK growth in Wave bioreactors as a function of time for fed-batch and perfusion runs.
Figure 10:
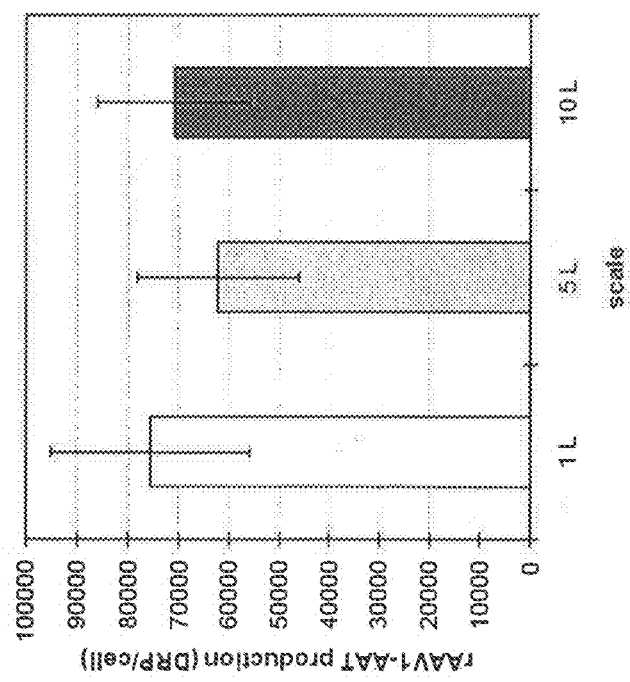
FIG. 10 is a graph that shows typical rAAV1-AAT specific yields (DRP/cell) for Wave disposable bioreactor vector production at 1/2 L (49 hpi. n=3. rHSV-rep2cap1 MOI of 12 and rHSV-AAT MOI of 2), 5/10 L (24 hpi, n=4. rHSV-rep2cap1 MOI of 4 and rHSV-AAT MOI of 2), and 10/20 L (24 hpi, n=6, rHSV-rep2cap1 MOI of 4 and rHSV-AAT MOI of 2) culture scales.
Figure 11:
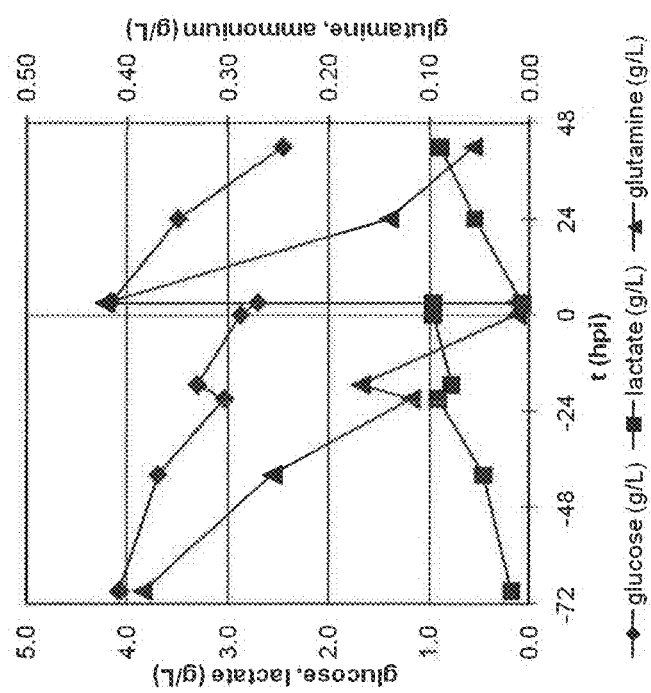
FIG. 11 is a graph that shows metabolite concentrations during a 1 L fed-batch sBHK rAAV1-AAT production run, pre- and post-infection.
Figure 12:
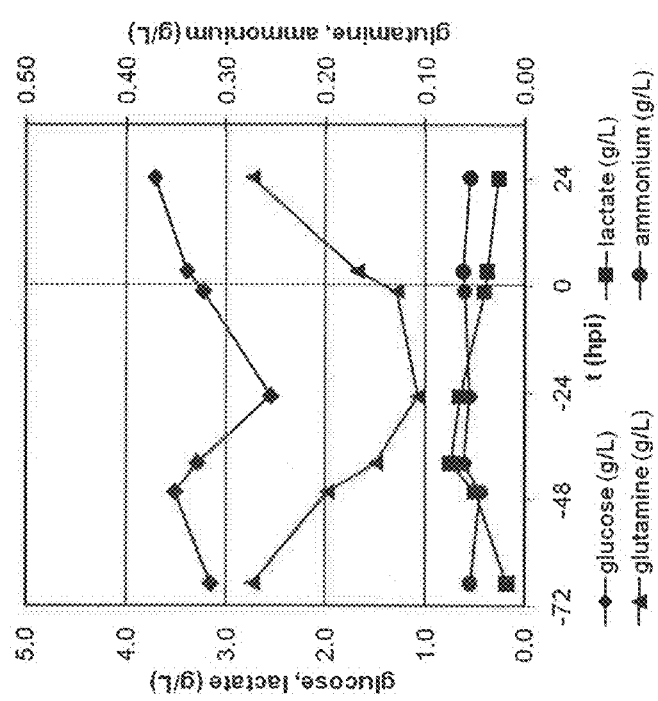
FIG. 12 is a graph that shows typical metabolite concentrations during a 1 L perfusion sBHK rAAV1-AAT production run, pre- and post-infection.
Figure 13:
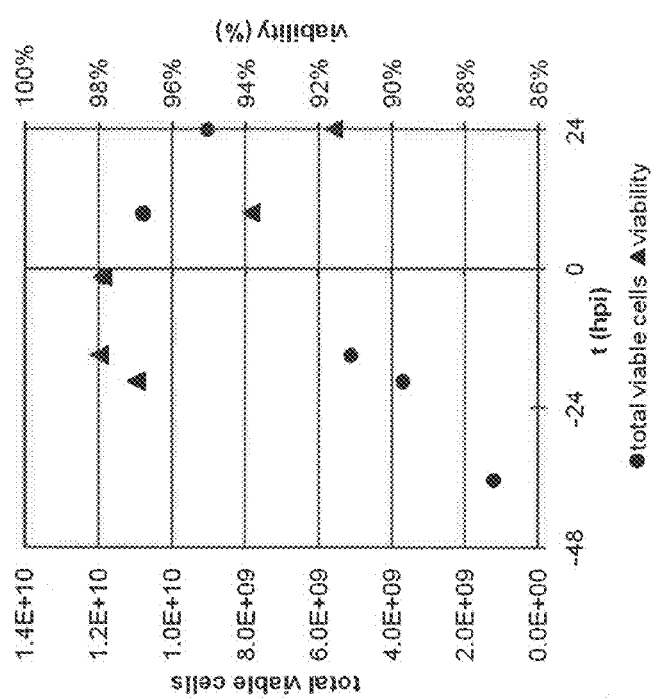
FIG. 13 is a graph that shows typical cell growth and viability for a 5 L culture volume Wave bioreactor batch run.
Figure 14:
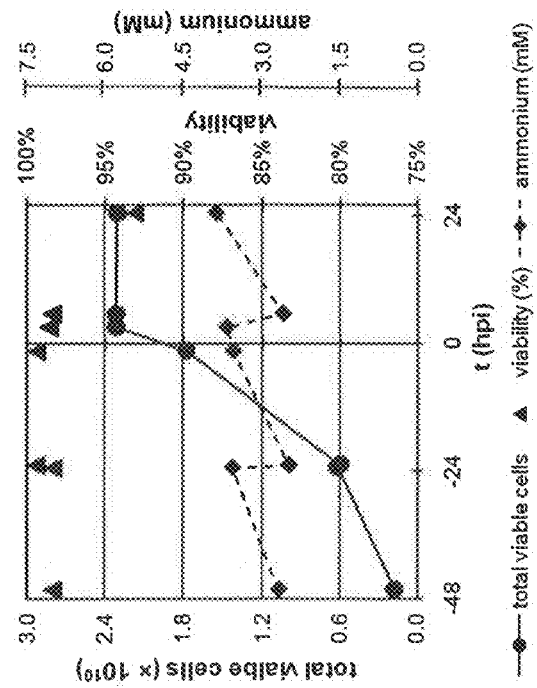
FIG. 14 is a graph that shows typical cell growth, viability, and ammonium concentrations for a 10 L culture volume Wave bioreactor batch run.

Initially, sBHK rAAV2-GFP production was scaled to Celligen Plus continuous stirred tank reactors (CSTR) in DMEM supplemented with 5% FBS. The pH set point was 7.2, the dissolved oxygen (D.O.) set point was 50% of air saturation, and the agitation set point, using marine impellers, was 100 rpm, in a 3.5 L working volume, 5.0 L total volume jacketed glass vessel equipped with spin filters for cell retention. Reactors were seeded between $1.3$-$2.5 \times 10^5$ cells/mL and grown to $1.2$-$1.4 \times 10^6$ cells/mL and co-infected with rHSV-rep2cap2 (MOI of 12) and rHSV-GFP (MOI of 2) to produce rAAV2-GFP. FIG. 7 shows the results. Media was exchanged at 2 hpi for DMEM lacking FBS, via tangential flow filtration using a hollow fiber filter device for cell retention. The run was repeated (as described above), and FIG. 8 shows similar results.

rAAV production was also scaled to 1 L/2 L (working volume/total volume) Wave disposable bioreactors. The pH set point was 7.2, the agitation rate was 20 rocks/min, the rocking angle was 7°, and total gas flow varied between 0.1 and 0.3 L/min. Bioreactors were seeded with an initial volume of 1.0 L at a density of $1.0$-$2.5 \times 10^5$ cells/mL. Cells were grown in fed-batch (run 1, 2, 3) or perfusion (run 4, 5) to prevent nutrient depletion, and pre-infection cell growth as a function of time in 1 L/2 L Wave disposable bioreactors is shown in FIG. 9. The average doubling time was 13.5 h. Fed-batch runs had a bolus of 5×DMEM added at 25-52 hps, and perfusion run feeding with DMEM initiated 29-42 hps, to prevent nutrient depletion as needed. Runs 1, 2, and 3 were co-infected with rHSV-rep2cap1 (MOI of 12) and rHSV-AAT (MOI of 2) to produce rAAV1-AAT, and resulted in a specific productivity of 75,600 DRP/cell. The results are shown in FIG. 10 (1 L scale data point, n=3). Run 5 was co-infected with the same vectors, but at a MOI of 4 and 2, respectively, based on flask data which showed rAAV1-AAT production to be insensitive to rHSV-rep2cap1 MOI between 4 and 12 and resulted in 19.252 DRP/cell by 24 hpi. Maximum cell densities for fed-batch runs were between $1.6 \times 10^6$ and $2.3 \times 10^6$ cells/mL while perfusion runs achieved a maximum density $1.2 \times 10^7$ cells/mL at non-constant volume, prior to infection, as shown in FIG. 9. Media exchange prior to infection was accomplished by centrifugation for fed-batch runs. FIG. 11 shows typical metabolite concentrations for 1 L Wave fed-batch runs. FIG. 12 shows metabolite concentrations for a typical 1 L perfusion run.

sBHK rAAV batch production was also scaled to 5 and 10 L culture volumes in 10 L/20 L (working volume/total volume) Wave bioreactors using a rHSV-rep2cap1 at an MOI of 4 and a rHSV-AAT at an MOI of 2. Cells were grown as in 1 L Wave bioreactor cultures, with (10 L) or without (5 L and 10 L) media exchange. Media exchanged cultures grew to higher terminal cell densities since nutrients were replenished. Terminal cell densities with media exchange during growth achieved $3.1 \times 10^6$ cells/mL prior to infection, while $2.3 \times 10^6$ cells/mL was achieved without media exchange during growth. FIG. 13 shows a typical 5 L Wave disposable bioreactor culture without media exchange that resulted in a pre-infection cell density of $2.3 \times 10^6$ cells/mL. FIG. 10 shows rAAV1-AAT production for 5 L (data point 2, n=4) and 10 L (data point 3, n=6) culture volume Wave bioreactor runs, and demonstrates that specific productivity (DRP/cell) was maintained during scale up from 1 L to 10 L of rAAV production in suspension-adapted cells. FIG. 14 is a graph that shows typical sBHK cell growth at the 10 L culture volume scale in Wave bioreactor runs resulting in average doubling times of 13.1 h. FIG. 14 demonstrates that spinner flask, and 1 L Wave bioreactor cell growth rates were successfully scaled to 10 L Wave bioreactor production volumes while maintaining similar growth rates without inhibition from ammonium accumulation (Christie, A., and Butler, M.; 1999, The adaptation of BHK cells to a non-ammoniagenic glutamate-based culture medium. Biotechnol Bioeng 64, 298-309).

Taken together, the results presented herein described a scalable method for producing recombinant AAV viral particles in a mammalian cell capable of growing in suspension.

Other Embodiments

From the foregoing description, it will be apparent that variations and modifications may be made to the invention described herein to adopt it to various usages and conditions. Such embodiments are also within the scope of the following claims.

All patents and publications mentioned in this specification are herein incorporated by reference to the same extent as if each independent patent and publication was specifically and individually indicated to be incorporated by reference.

What is claimed is:

1. A method for producing recombinant AAV viral particles, the method comprising:
co-infecting a suspension BHK cell with a first recombinant herpesvirus comprising a nucleic acid encoding an AAV rep and an AAV cap gene each operably linked to a promoter; and a second recombinant herpesvirus comprising a gene of interest, and a promoter operably linked to said gene of interest;
wherein said cell is infected at a combined multiplicity of infection (MOI) of between 3 and 14; and
allowing the cell to produce the recombinant AAV viral particles, thereby producing the recombinant AAV viral particles.

2. The method of claim 1, wherein the gene of interest is a therapeutic gene.

3. The method of claim 2, wherein the therapeutic gene is selected from the group consisting of: an inhibitor of anti-angiogenic genes, an alpha-1 antitrypsin gene, a retinoschisin gene, an acid alpha glucosidase gene, a RPE65 gene, a beta-subunit of the cone photoreceptor cGMP-gated channel (CNGB-3) gene, an alpha-subunit of the cone photoreceptor cGMP-gated channel (CNGA-3) gene, a cone photoreceptor G-protein alpha-subunit (GNAT2) gene, a Retinal pigment epithelium-specific 65 kDa (RPE65) gene, a X-linked juvenile retinoschisis (RS1) gene, a Brain-derived neurotrophic factor (BDNF) gene, a Glial cell-derived neurotrophic factor (GDNF) gene, a Myotonic dystrophy protein kinase (DMPK) gene, a CCHC-type zinc finger gene, a nucleic acid binding protein (known as CNBP or ZNF9) gene, a Retinitis pigmentosa GTPase regulator (RPGR) gene, an Acid α-glucosidase (GAA) gene, a Choroideremia (CHM) gene, a Rab escort protein-1 (REP1) gene, an Alpha-synuclein (SNCA) gene, a Coagulation factor VIII gene, a procoagulant component (hemophilia A) gene, a procoagulant component (F8) gene, a Coagulation factor IX gene, a plasma thromboplastic component gene, a Coagulation factor IX of Christmas disease gene, a Coagulation factor IX of hemophilia B gene, a Coagulation factor IX of F9 gene, an Aryl hydrocarbon receptor interacting protein-like 1 (AIPL1) gene, a X-linked Inhibitor of Apoptosis Protein (XIAP) gene, a clarin-1 (CLRN1) gene, a Leber's hereditary neuropathy gene, a MT-ND1 gene, a MT-ND4 gene, a MT-ND4L gene, a MT-ND6 gene, an alpha-galactosidase A (α-Gal A) gene and an Alpha-L-iduronidase gene.

4. The method of claim 1, wherein the cap gene is selected from an AAV with a serotype selected from the group consisting of AAV-1, AAV-2, AAV-3, AAV-4, AAV-5, AAV-6, AAV-7, AAV-8, AAV-9, and rh-AAV-10.

5. The method of claim 1, wherein the first herpesvirus and the second herpesvirus are viruses selected from the group consisting of: cytomegalovirus (CMV), herpes simplex (HSV) and varicella zoster (VZV) and epstein barr virus (EBV).

6. The method of claim 5, wherein the herpesvirus is replication defective.

7. The method of claim 1 wherein the co-infection is simultaneous.

8. A method for producing recombinant AAV viral particles in a mammalian cell, the method comprising:
co-infecting a suspension BHK cell with a first recombinant herpesvirus comprising a nucleic acid encoding an AAV rep and an AAV cap gene each operably linked to a promoter; and a second recombinant herpesvirus comprising a gene of interest, and a promoter operably linked to said gene of interest;
wherein said cell is infected at a combined multiplicity of infection (MOI) of between 3 and 14; and
allowing the cell to propagate,
thereby producing the recombinant AAV viral particles, whereby the number of viral particles produced is equal to or greater than the number of viral particles grown in an equal number of cells under adherent conditions.

9. A method for delivering a nucleic acid sequence encoding a therapeutic protein to a suspension BHK cell, the method comprising:
co-infecting the BHK cell with a first recombinant herpesvirus comprising a nucleic acid encoding an AAV rep and an AAV cap gene each operably linked to a promoter; and a second herpesvirus comprising a gene of interest, wherein the gene of interest comprises a therapeutic protein coding sequence, and a promoter operably linked to said gene of interest; and
wherein said BHK cell is infected at a combined multiplicity of infection (MOI) of between 3 and 14; and
allowing the virus to infect the BHK cell and express the therapeutic protein,
thereby delivering the nucleic acid sequence encoding the therapeutic protein to the BHK cell.

* * * * *